(12) United States Patent
Gicquel et al.

(10) Patent No.: US 6,261,568 B1
(45) Date of Patent: Jul. 17, 2001

(54) ATTENUATED RECOMBINANT MYCOBACTERIA USEFUL AS IMMUNOGENS OR AS VACCINE COMPONENTS

(75) Inventors: Bridgitte Gicquel, Paris; Christophe Guilhot, Issy les Moulineaux; Mary Jackson, Paris, all of (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/095,801

(22) Filed: Jun. 11, 1998

Related U.S. Application Data

(60) Provisional application No. 60/049,390, filed on Jun. 11, 1997.

(51) Int. Cl.$^7$ .............................. A61K 39/02; C12Q 1/68; C07K 1/00; C07H 21/04

(52) U.S. Cl. .................................... 424/200.1; 424/248.1; 435/6; 435/91.1; 435/91.2; 435/253.1; 530/350; 536/24.32; 536/24.33

(58) Field of Search .............................. 424/248.1, 200.1; 435/6, 91.1, 91.2, 253.1; 530/350; 536/24.32, 24.33

(56) References Cited

PUBLICATIONS

Jackson et al., "The *Mycobacterium tuberculosis* Purine Biosynthetic Pathway: Isolation and Characterization of the purC and purL Genes," Microbiology, vol. 142, pp. 2439–2447 (1996).

Pelicic et al., "Generation of Unmarked Directed Mutations in Mycobacteria, Using Sucrose Counter–Selectable Suicide Vectors," Molec. Microbio., vol. 20(5), pp. 919–925 (1996).

Straley et al., "Growth in Mouse Peritoneal Macrophages of *Yersinia pestis* Lacking Established Virulence Determinants," Infection and Immunity, vol. 45(3), pp. 649–654, (1984).

Noriega et al., "Construction and Characterization of Attenuated ΔaroA ΔvirG *Shigella flexneri* 2a Strain CVD 1203, a Prototype Live Oral Vaccine," Infection and Immunity, vol. 62(11), pp. 5168–5172 (1994).

Oyston et al., "Immunization with Live Recombinant *Salmonella typhimurium aroA* Producing F1 Antigen Protects Against Plague," Infection and Immunity, vol. 63(2), pp. 563–568 (1995).

Hoiseth et al., Aromatic–dependent *Salmonella typhimurium* Are Non–virulent and Effective as Live Vaccines, Nature, vol. 291, pp. 238–239 (1981).

Levine et al., "Safety, Infectivity, Immunogenicity, and In Vivo Stability of Two Attenuated Auxotrophic Mutant Strains of *Salmonella typhi*, 541Ty and 543Ty, as Live Oral Vaccines in Humans," J. Clin. Invest. vol. 79, pp. 888–902 (1987).

Wheeler, "Biosynthesis and Scavenging of Pyrimidines by Pathogenic Mycobacteria," J. General Microbio., vol. 136, pp. 189–201 (1990).

Masood et al., Role of Various Carbon and Nitrogen Sources in The Regulation of Enzymes of Pyrimidine Biosynthesis in *Mycobacterium smegmatis* TMC 1546, Ann. Inst. Pasteur/ Microbiol., vol. 138, pp. 501–507 (1987).

Wheeler, "Pyrimidine Biosynthesis de Novo in *M. leprae*," FEMS Microbiology Letters, vol. 57, pp. 185–190 (1989).

Wheeler, "Pyrimidine Biosynthesis in *Mycobacterium leprae* and Other Intracellular Mycobacteria," Acta Leprologica, vol. 7 (1), pp. 33–35 (1989).

Wheeler, "Biosynthesis and Scavenging of Purines by Pathogenic Mycobacteria Including *Mycobacterium leprae*," J. General Microbiology, vol. 133, pp. 2999–3011 (1987).

Wheeler, "Session 1: Biochemistry: Biosynthetic Pathways in *Mycobacterium leprae*," Acta Leprologica, vol. 7(1), pp. 21–24 (1989).

McFarland et al., "Effect of Different Purine Auxotrophic Mutations on Mouse–Virulence of a Vi–positive Strain of *Salmonella dublin* and of Two Strains of *Salmonella typhimurium*," Microbial Pathogenesis, vol. 3, pp. 129–141 (1987).

Meyer et al., "Purification and Characterization of the purE, purK and purC Gene Products: Identification of a Previously Unrecognized Energy Requirement in the Purine Biosynthetic Pathway," Biochemistry, vol. 31, pp. 5022–5032 (1992).

Ebbole et al., "Cloning and Characterization of a 12–gene Cluster from *Bacillus subtilis* Encoding Nine Enzymes for de Novo Purine Nucleotide Synthesis," J. Biol. Chem., vol. 262(17), pp. 8247–8287 (1987).

Gu et al., "Isolation and Complete Sequence of the purL Gene Encoding FGAM Synthase II in *Lactobacillus casei*," Gene, vol. 119, pp. 123–126 (1992).

Pelicic et al., "Efficient Allelic Exchange and Transposon Mutagenesis in *Mycobacterium tuberculosis*," Proc. Natl. Acad. Sci., USA, vol. 94, pp. 10955–10960 (1997).

Meng et al., "Autoregulation of PurR Repressor Synthesis and Involvement of purR in the Regulation of purB, purC, purL, purMN and guaBA Expression in *Escherichia coli*," Eur. J. Biochem., vol. 187, pp. 373–379 (1990).

*Primary Examiner*—Rodney P. Swart
(74) *Attorney, Agent, or Firm*—Finnegan, Henderson, Farabow, Garrett & Dunner, L.L.P.

(57) ABSTRACT

This invention provides recombinant mycobacterium strains of pathogenic origin that have been attenuated by the inactivation of a gene coding for a metabolic protein, specifically a gene coding for a protein necessary for the biosynthesis of a purine or a pyrimidine base, and more precisely, the purC gene that codes for an enzyme of the metabolic pathway of purine biosynthesis. The recombinant mycobacterium of this invention have a reduced capacity to propagate in a mammalian host, but remain viable in the host for a period of time sufficient to induce an protective immune response against the natural pathogenic mycobacterium counterpart.

3 Claims, 11 Drawing Sheets

PLASMID NAME: p27CKX
PLASMID SIZE: 14.40 kb
CONSTRUCTED BY: MARY JACKSON
CONSTRUCTION DATE: 16/03/96
COMMENTS: VECTEUR THERMOSENSIBLE SacB/Xy1E POUR
LA RECOMBINAISON HOMOLOGUE AVEC LE GÈNE
purC de M. TUBERCULOSIS

ATTENUATED RECOMBINANT MYCOBACTERIA USEFUL AS IMMUNOGENS OR AS VACCINE COMPONENTS

This application claims benefit of provisional application No. 60/049,390 filed Jun. 11, 1997.

BACKGROUND OF THE INVENTION

The concept of using attenuated pathogenic bacteria as a vaccine component has been widely disclosed and practiced. The methods for obtaining such attenuated bacteria involve selecting random mutants by chemically- or irradiation-induced mutants or producing recombinant bacteria of pathogenic origin in which a gene involved in some metabolic pathway of the bacteria has been inactivated by genetic engineering.

Straley et al. (1984) have studied the survival of mutant avirulent *Yersinia pestis* that carry defects in one or several metabolic pathways.

Noriega et al. (1994) have genetically engineered an oral *Shigella* strain for use as a vaccine prototype by introducing deletions in a gene (aroA) coding for a protein involved in the metabolic pathway of the aromatic amino acids and have demonstrated that the defective recombinant resultant *Shigella* strains were able to induce protective antibodies against the wild pathogen.

Substantial work has been also done using Salmonella as a model. See, for example the reports of Hoiseth et al. (1981), Levine et al. (1987), Oyston et al. (1995) and Curtiss (1990).

However, similar work has not yet been done for *Mycobacterium tuberculosis*, the etiologic agent of tuberculosis (TB), which infects one-third of the world's population and kills 3 million people each year. TB is the largest cause of death in the world caused by a single infectious organism (Bloom and Murray, 1992). According to the WHO, more people died from TB in 1995 than in any other year in history. Worldwide, 60 million people suffer from active TB and annually 7 million new cases arise (Dolin et al., 1994). It has been estimated that, at current rates, up to half a billion people will suffer from TB in the next 50 years.

Efficient chemotherapy exists but requires lengthy and expensive treatments, making its widespread use and control difficult to achieve in developing countries. Prophylactic vaccination against tuberculosis with the attenuated stain of bovine mycobacteria, BCG (*Mycobacterium bovis* Bacillus Calmette—Guérin), is more cost effective and has indeed been employed worldwide. Although BCG vaccination has provided protection against tuberculosis in certain populations, the variation in efficacy of this vaccine in different field trials and its modest protective effect against the adult form of the disease (estimated by meta-analysis to be about 50%) (Colditz et al., 1994) are points of major concern. These considerations have led the WHO to place TB control efforts, notably through the development of new vaccines, among its top priorities.

However, despite its importance, the genetic determinants of *M. tuberculosis* virulence remain poorly characterized. In the recent years, considerable efforts have been made towards the identification of individual mycobacterial antigens involved in the immune response to tuberculosis (Young et al., 1992) with the aim of developing subunit vaccines. The observation that only live vaccines confer high levels of protective immunity against tuberculosis (Weiss & Dubos, 1955; Orme, 1988), in addition to the fact *M. tuberculosis* short-term culture filtrates containing proteins secreted by actively replicating bacteria were shown to protect mice against a subsequent challenge with the virulent strain (Andersen, 1994), suggested that proteins secreted by *M. tuberculosis* might be good candidates for the design of subunit vaccines. Indeed, antigens such as ESAT 6 (Andersen et al., 1995), mpt64 (Haslov et al., 1995), the antigen from the 45/47 kDa complex (Romain et al., 1993) and the components of the antigen 85 complex (Wiker & Harboe, 1992) were identified as powerful immunogens eliciting delayed-type hypersensitivity (Haslov et al., 1995; Romain et al., 1993), antibody responses (Romain et al., 1993; Wiker & Harboe, 1992) and the proliferation of T-lymphocyte populations responsible for long-lived immunity (Andersen et al., 1995) in guinea pigs or mice. Some of these antigens showed protective efficacy in the mouse model of tuberculosis when used as DNA vaccines (Huygen et al., 1996).

An alternative strategy to develop novel vaccines consists of constructing mutant strains of mycobacteria that are rationally attenuated. The recent development of genetic tools for performing site-specific (Pelicic et al., 1997) and random-site mutagenesis (Pelicic et al., 1997; Bardarov et al., 1997) in organisms from the *Mycobacterium tuberculosis* complex now renders feasible the accomplishment of such a goal. Live vaccines should have advantages over subunit vaccines in that i) they represent a greater pool of antigens which presumably should cover a wider range of T-cell repertoires, and ii) they are generally more cost effective to produce. Moreover, attenuated mutants of *M. tuberculosis* should express homologous protective antigens which the BCG strains lack, and, thus, elicit a more specific and stronger protective immune response against virulence challenge. In support of this hypothesis, the molecular analysis by Mahairas and collaborators (1996) of genetic differences between *M. bovis* BCG and its virulent counterparts *M. bovis* and *M. tuberculosis* clearly established the existence of regions of deletion in the genome of BCG (representing about 30 kb in all), some of which contain the ORFs encoding the highly immunogenic ESAT 6 and mpt64 antigens (the latter being absent from certain BCG strains only (Oettinger & Andersen, 1994)).

Among attenuated strains of intracellular bacterial pathogens, auxotrophic mutants carrying defects in the shikimate or the purine biosynthetic pathways were shown to be of particular interest as potential live vaccines candidates because they are attenuated in vivo and have the ability to retain their immunogenicity. Some *Salmonella*, *Yersinia* and *Corynebacteria* purine and aromatic amino acid auxotrophs have LD50s in mice 3 to 6 $\log_{10}$ higher than that of the wild type (Hoiseth & Stocker, 1981; O'Callaghan et al., 1988; McFarland & Stocker, 1987; Bowe et al., 1989; Simmons et al., 1997). These *Salmonella* auxotrophs as well as a *Brucella purE* deficient mutant are, however, able to persist several weeks in mice (Crawford et al., 1996; O'Callaghan et al., 1988) and the aroA and purA mutants of *Salmonella typhimurium* are able to induce protective immunity in mice against a challenge with the virulent strain (Hoiseth & Stocker, 1981; McFarland & Stocker, 1987).

However, the extreme difficulty in creating defined mutants of *M. tuberculosis*, either by allelic exchange or transposon mutagenesis, has prevented identification of its virulence factors following Koch's postulates (Falkow, 1988; Jacobs, 1992). Rather, alternative genetic strategies have been used, including complementation of non-pathogenic bacteria (Arruda et al, 1993) and spontaneous avirulent mutants with libraries of virulent *M. tuberculosis*

(Pascopella et al. 1994) or *M. bovis* (Collins et al., 1995) chromosomal DNA. Although these studies have identified genes required for entry into epithelial cells and conferring a growth advantage in vivo, the great majority of the mycobacterial genes involved in virulence remain unknown. Developing efficient mutagenesis systems is thus a top priority for mycobacterial genetics.

One method for creating mutants is allelic exchange mutagenesis. Recently, low-frequency allelic exchange was demonstrated in bacteria of the *M. tuberculosis* complex using a suicide delivery vector (Reyrat et al., 1995; Azad et al., 1996), and new protocols allowing easier detection of allelic exchange mutants have also been developed Norman et al., 1995; Balasubramamian et al., 1996; Pelicic et al., *FEMS Microbiol. Lett.* 1996). However, detection of very rare allelic exchange events is hindered by low transformation efficiencies and high frequencies of illegitimate recombination. Thus, many mycobacterial genes still remain refractory to allelic exchange by available technology.

Clearly, the allelic exchange mutagenesis system requires the design of more efficient methods. The problems encountered can be circumvented by using a replicative delivery vector which is efficiently lost under certain conditions. Allowing the introduced delivery vector to replicate avoids the problems arising from low transformation efficiencies. Then, under counter-selective conditions, clones that still contain the vector are eliminated, allowing the detection of very rare genetic events. One such system has recently been developed. Using a conditionally replicative vector which is efficiently lost at 39° C. in *M. smegmatis*, the first mycobacterial insertional mutant libraries were constructed in this fast-growing model strain (Guilhot et al., 1994). However, the thermosensitive vectors used are only weakly thermosensitive in slow-growing mycobacteria of the *M. tuberculosis* complex and therefore cannot be used in these species for allelic exchange mutagenesis (unpublished data).

To date, it has not been possible to inactivate any specific gene of a mycobacterium strain via allelic exchange due to the absence of an efficient positive counter-selective marker gene that allows for selection of recombinant mycobacteria carrying a defective metabolic pathway gene. Thus, it has not previously been possible to generate a mycobacterium strain with an inactivated gene, particularly a gene involved in a metabolic pathway of the pathogenic mycobacteria, such that the defective strain is able to replicate only at a very low level in the host but does persist in the host long enough to allow the induction of an immune response. Nor has it been possible to produce an attenuated recombinant mycobacterium strain that is incapable of inducing disease in a host to which it has been administered.

SUMMARY OF THE INVENTION

This invention provides for the first time, recombinant mycobacterium strains of pathogenic origin that have been attenuated by the inactivation of a gene coding for a metabolic protein, specifically a gene coding for a protein necessary for the biosynthesis of a purine or a pyrimidine base, and more precisely, the purC gene that codes for an enzyme of the metabolic pathway of purine biosynthesis.

Construction of recombinant mutant auxotrophs of *Mycobacterium* via an allelic exchange event has allowed the isolation of new live attenuated strains of *M. tuberculosis* of immunogenic and/or vaccinal value. Using the purC gene from *M. tuberculosis* (Jackson et al., 1996), auxotrophic mutants for the purine bases of *M. bovis*-BCG (vaccinal Pasteur strain number 1173P2, which is publicly available at the Pasteur Institute Collection) and of *M. tuberculosis* (clinical isolate Mt103) have been constructed via an allelic exchange event.

Thus, it is an object of this invention to provide recombinant mycobacterium of pathogenic origin that have a lower capacity to propagate in a mammalian host, specifically a human, but which remain viable in the host for a period of time sufficient to induce an immune response, and preferably, a protective immune response, against the natural pathogenic mycobacterium counterpart.

It is a further object of this invention to provide attenuated recombinant mycobacterium incapable of inducing a disease in a host to which they have been administered.

*Mycobacterium* species, as described herein, may be any strain of the *Mycobacterium* genus, including, but not limited to: *Mycobacterium tuberculosis* complex such as *M. Bovis*-BCG, *M. bovis, M. tuberculosis, M. africanum* and *M. microti; M. avium; M. intracellulare;* and *Mycobacterium leprae*.

Figure 10A:
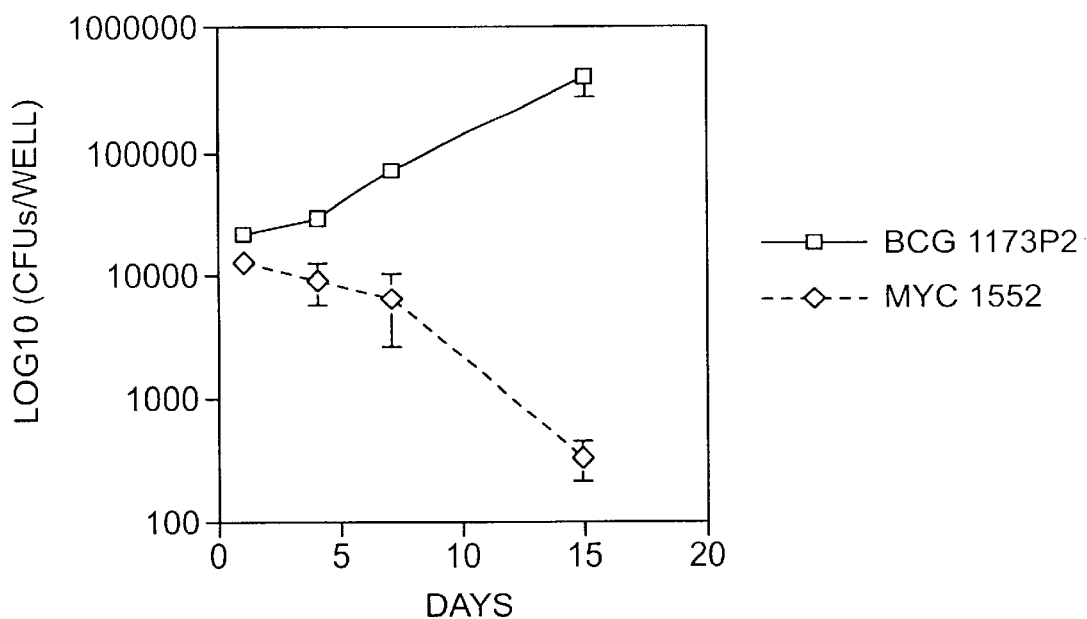
Figure 10B:
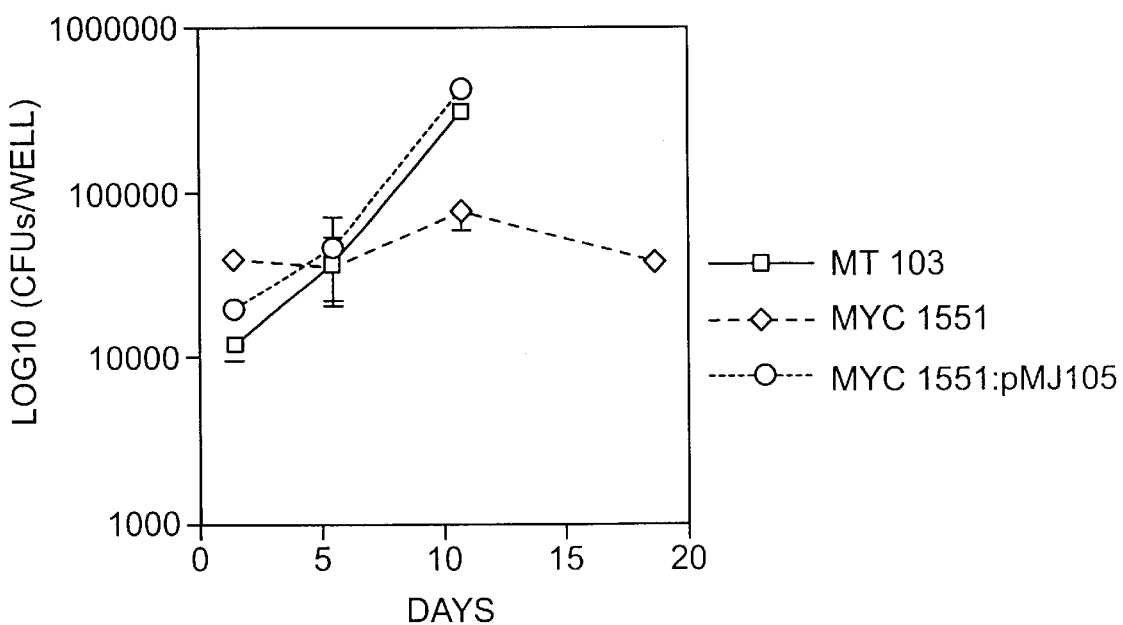

FIG. 10 depicts the persistence of MYC1551 and MYC1552 within bone-marrow macrophages. In this representative experiment, $5 \times 10^4$ macrophages were infected with $5 \times 10^4$ viable bacilli and the growth was measured over time. *M. bovis* BCG 1173 P2 (-□-), or the BCG auxotroph (MYC1552) ( . . . ◊ . . . ) were used to infect the macrophages (FIG. 10A). A *M. tuberculosis* virulent strain (MT103) (-□-), its auxotroph counterpart (MYC1551) ( . . . ◊ . . . ) or MYC1551 harbouring the plasmid pMJ105 (carrying the purC gene) ( . . . ○ . . . ) were used to infect the macrophages (FIG. 10B). Each point represents the geometric mean +/− the standard deviation (SD) of two independant cultures.

Figure 11A:
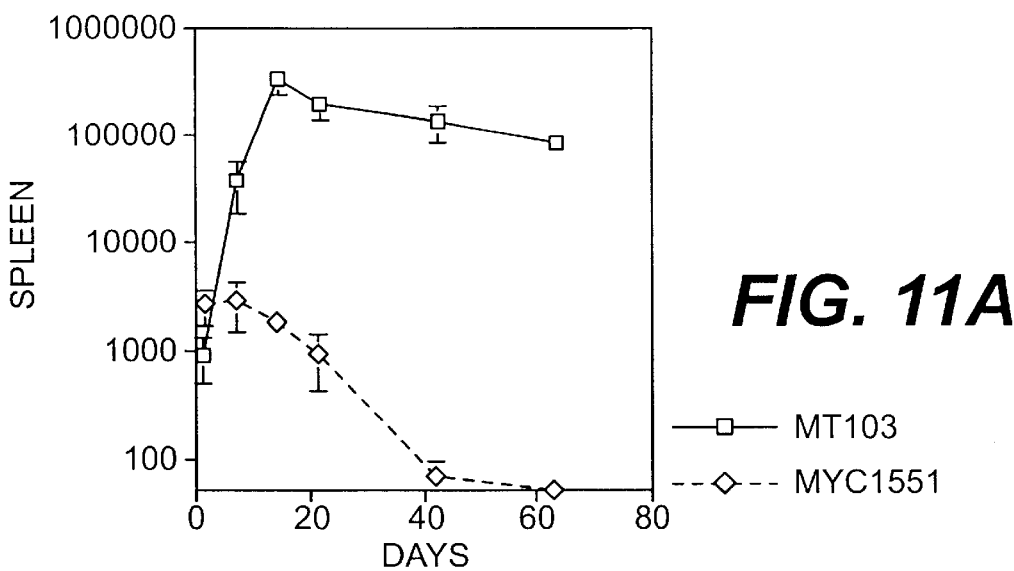
Figure 11B:
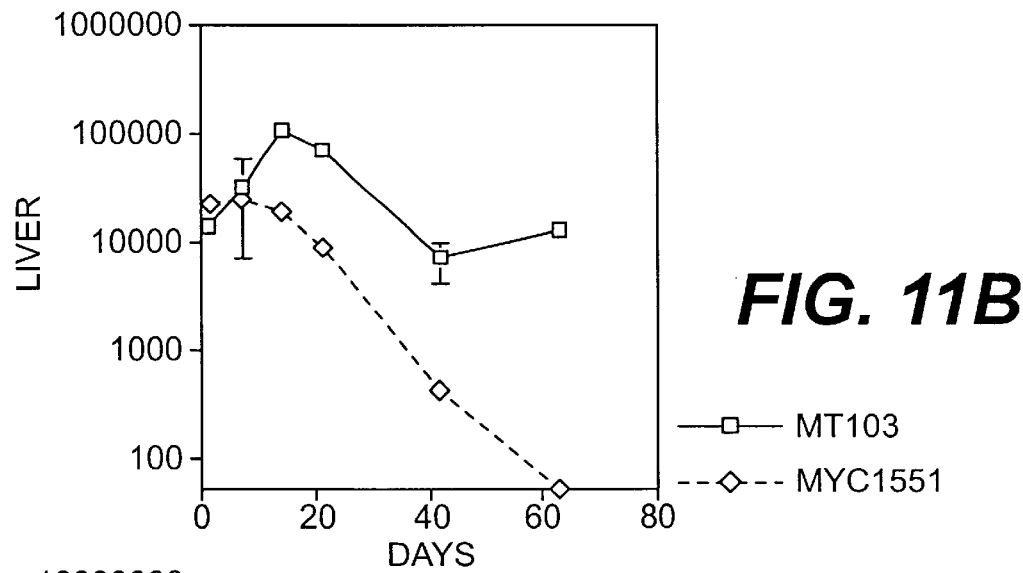
Figure 11C:
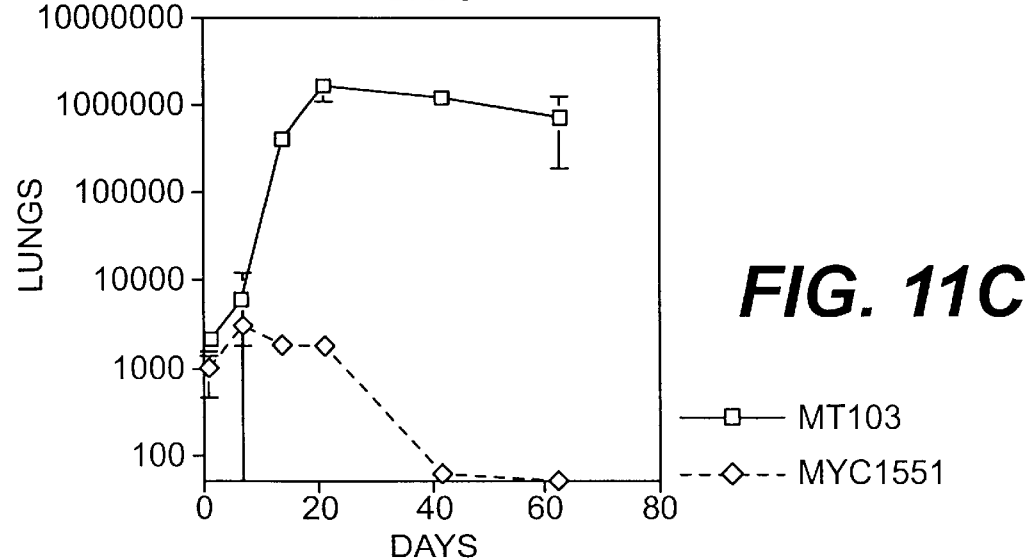

FIG. 11 depicts persistence of *M. tuberculosis* MT103 and the purine auxotroph MYC1551 in mice. BALB/c mice were infected intravenously with $10^7$ viable units of either a *M. tuberculosis* virulent strain (MT103) (-□-) or MYC1551 ( . . . ◊ . . . ), and the persistence of bacteria in three organs, spleen (FIG. 11A), liver (FIG. 11B), and lung (FIG. 11C) were measured over time. The value indicated represents the geometric mean+SD obtained with five different mice.

Figures 12A, 12B, 12C:
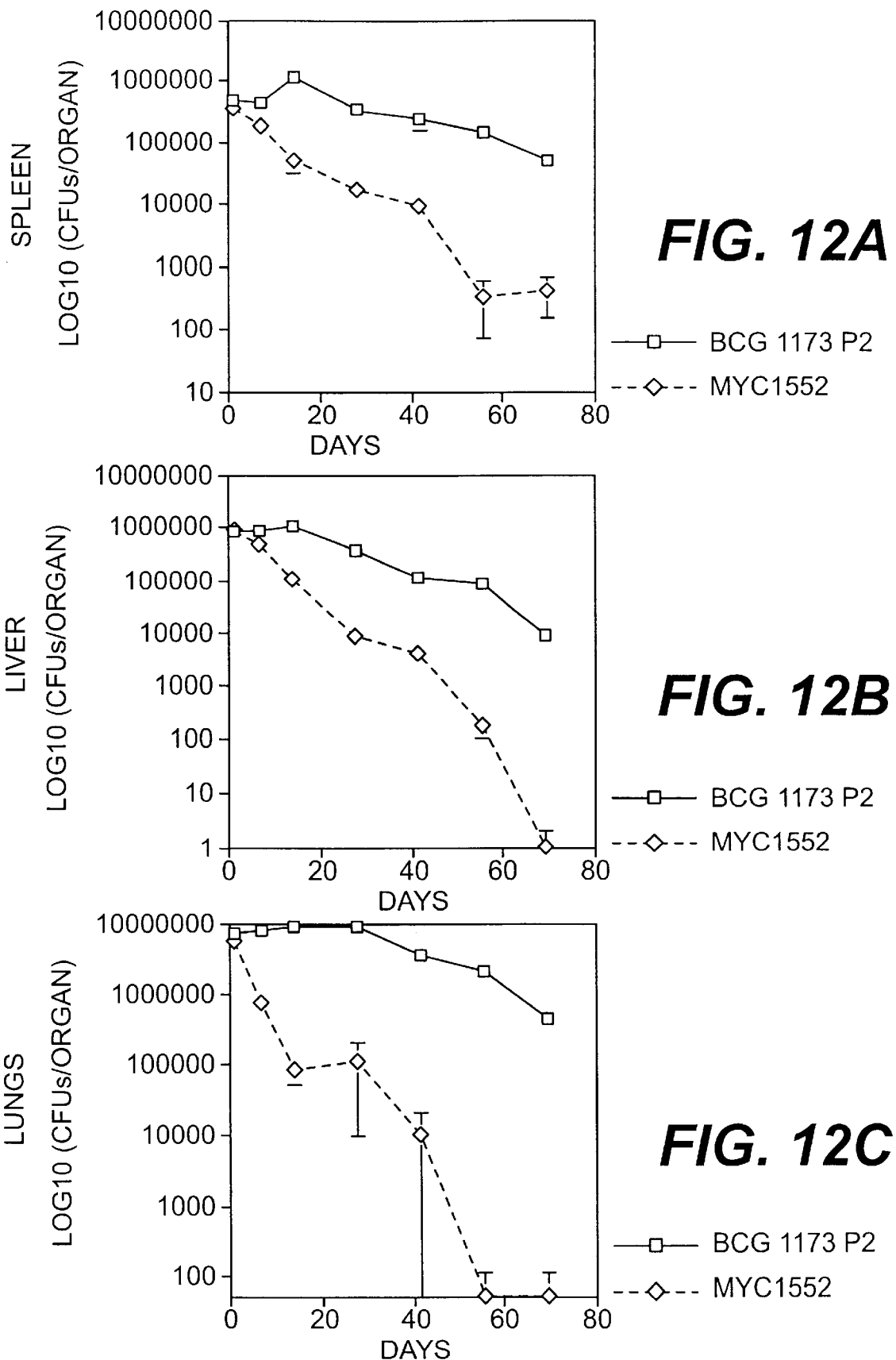

FIG. 12 depicts persistence of *M. bovis* BCG and its auxotroph counterpart, MYC1552, in mice. BALB/c mice were infected intravenously with $10^7$ viable units of either *M. bovis* BCG (-□-) or MYC1552 ( . . . ◊ . . . ), and the persistence of bacteria in three organs, spleen (FIG. 12A), liver (FIG. 12B), and lung (FIG. 12C) were measured over time. The value indicated represents the geometric mean+SD obtained with five different mice.

DETAILED DESCRIPTION

A better understanding of *Mycobacterium tuberculosis* virulence mechanisms is highly dependent on the design of efficient mutagenesis systems. A system enabling the positive selection of insertional mutants having lost the delivery vector has now been developed. This system is efficient for gene exchange mutagenesis and has been demonstrated with the purC gene: 100% of the selected clones were allelic exchange mutants. Therefore, a single, simple methodology has enabled the development of powerful mutagenesis systems, the lack of which has previously been a major obstacle to the genetic characterization of *M. tuberculosis*.

Thus, using the allelic exchange method of Pelicic et al. (*Mol. Microbiol.*, 1996) with an interrupted purC gene of *Mycobacterium tuberculosis,* it has been surprisingly discovered that the inactivation of the purC gene leads to recombinant *M. tuberculosis* strains that are still able to persist in a macrophage of a host, but have totally or partially lost their ability to replicate and lyse the macrophage in comparison with the corresponding wild strain. This surprising discovery has now enabled the design of new mycobacterial strains of pathogenic origin suitable as vaccine components.

The vectors used in this invention to select recombinant mycobacteria clones that have undergone an allelic exchange at the location of the gene of interest (i.e., the gene to be inactivated) are principally characterized by the following features:

a) the vector carries a conditional lethal counter-selective marker gene, for example the SacB gene, such as described in Pelicic et al., *Mol. Microbiol.* 1996;

b) the vector carries, preferably in the neighborhood of the conditional lethal counter-selection marker, an inactivated copy of the gene of interest (for example an interrupted gene involved in the biosynthesis of purine or pyrimidine bases, such as purC gene) that will replace its wild counterpart in the mycobacterial genome (chromosome or plasmid);

c) the vector optionally carries a conditionally functional origin of replication, such as a thermosensitive (ts) origin of replication which allows the control, during the allelic exchange method processing, of the vector replication; and d) the vector optionally carries an additional selection marker gene, preferably, an antibiotic resistance marker gene such as, for example, gentamycin, hygzomycin, or kanamycin resistance which may be used for preselecting the mycobacteria that have received the recombinant vector, whether they have undergone an allelic exchange event or not.

In the most preferred embodiment, this additional marker gene is inserted in the gene of interest in order to inactivate said gene of interest. FIG. 1 describes a preferred vector according to this invention, plasmid p27CKX.

In another preferred embodiment, the vector of this invention contains the SacB gene and a nucleotide sequence comprising a gene coding for a protein necessary for the biosynthesis of a purine or a pyrimidine base that has been inactivated by addition, deletion or substitution of at least one base pair and preferably from 10 to 20 base pairs. Preferably, the gene to be inactivated is a gene coding for guanine or adenine. Alternatively, the gene to be inactivated is a gene coding for a base selected from the group consisting of cytosine, uracil or thymine. In a more preferred embodiment, the gene to be inactivated is the purC gene or the purL gene.

In one embodiment of this invention, recombinant mutant mycobacteria, and specifically the purC mutant, of *M. tuberculosis* have been constructed following a selection protocol based on the use of the counter-selective marker gene SacB and of a thermosensitive conditional replication vector according to this invention.

In an optional pre-selection step of the selection protocol, mycobacteria that have received the recombinant vector are selected on a culture medium supplemented with an appropriate molecule, such as the corresponding antibiotic if the vector contains an antibiotic resistance marker gene.

Then, the mycobacteria or the pre-selected mycobacteria, are propagated at a permissive temperature in order to establish a high copy number (e.g., 3 to 5 copies) of the recombinant vector in every bacterium and generate a large number of bacteria carrying the recombinant vector. These conditions will greatly enhance the probability of an allelic exchange event occurring. In optimal conditions, the transfected mycobacteria may carry up to five recombinant vectors per bacterium cell.

Next, the mycobacteria are incubated in a medium supplemented with sucrose and at a non permissive temperature (to stop the recombinant vector replication). Because the mycobacteria are still multiplying when placed at a nonpermissive temperature, there is a dilution of the recombinant vector occurrence in the bacteria. Selecting bacteria that carry the antibiotic resistance gene will provide mainly mycobacteria that have the recombinant vector material inserted in their genome, either after an allelic exchange event, by a single cross-over in the purC locus, or by the random integration of the plasmid cassette in the mycobacterial genome. Simultaneously selecting bacteria that still propagate in a culture medium supplemented with sucrose will ensure that only the recombinant mycobacteria that have undergone an allelic exchange event and have lost the recombinant vector parts that carry the SacB gene survive. Thus, the combination of the ts gene action and the SacB gene action acts as a synergistic mechanism that allows selection of allelic exchange recombinant mycobacteria at a high rate.

Figure 1:
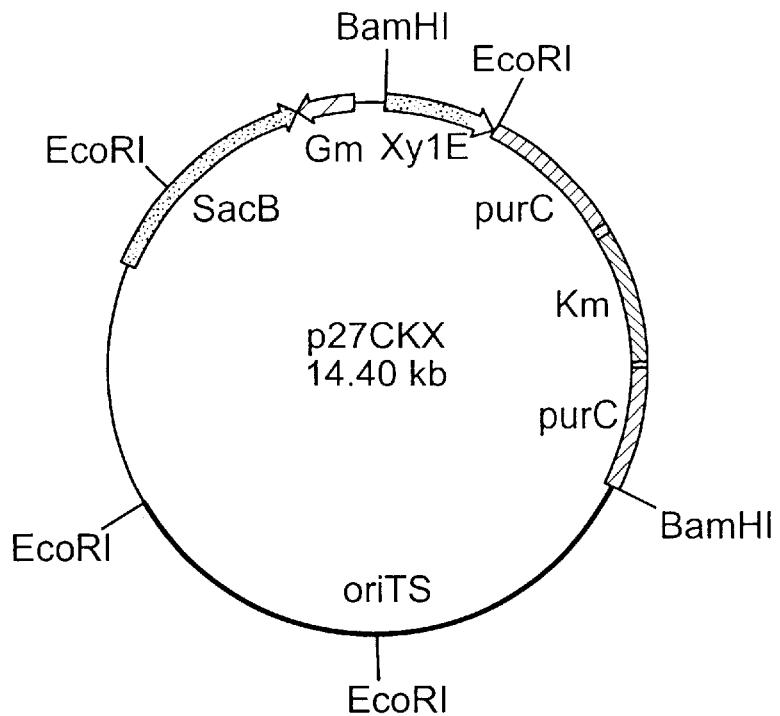
FIG. 1 depicts a map of plasmid p27CKX.

The resultant recombinant mycobacteria positively selected thus combine the features of having the recombinant gene of interest integrated in their genome but having lost the whole remaining recombinant vector sequences. These bacteria are then necessarily those which have undergone an allelic exchange event. Specifically, the purC recombinant auxotrophic mutant of *M. tuberculosis* has been constructed using plasmid p27CKX. A map of plasmid p27CKX is shown in detail in FIG. 1.

At the end of the different selection steps, 100% of the selected cfu (colony forming units) correspond to purC mutants of *M. tuberculosis*. This result has been confirmed by Southern blotting of 17 cfu (data not shown) and also by phenotypic assays (with minimum culture medium Sauton supplemented with hypoxanthin) on 96 cfu.

The intramacrophagic survival of the purC mutant of *M. tuberculosis* has been compared with the corresponding wild strain Mt103. Primary cultures of bone marrow macrophages from Balb/c mice have been infected with the wild or the recombinant auxotrophic strains of Mt103. The infection multiplicity was 40 for Mt103. At day 1, no difference was observed between the wild and the recombinant auxotrophic strains. At day 4, it was estimated that macrophages were infected by tenfold more with wild strains than with the auxotrophic recombinant strains. This difference, both in the proportion of infected macrophages and in the number of bacteria per macrophage cell increases with time. At day 8, the wild strain Mt103 had lysed almost all the cultured macrophages while for the recombinant auxotrophic strain Mt103 purC, the cell layer was not affected, with only 10 to 20% infected macrophages and 5 to 10 bacteria per cell. Thus, the auxotrophic recombinant strains have an intramacrophagic multiplication considerably decreased in comparison with the corresponding wild strains.

Accordingly, this invention pertains to a recombinant mycobacterium strain of pathogenic origin capable of replicating in the macrophage of a host, said strain containing in its chromosome or on a natural plasmid a gene coding for a protein necessary for the biosynthesis of a purine or a pyrimidine base that is inactivated by at least one point mutation or by addition, deletion or substitution of at least one base pair and preferably from 10 to 20 base pairs. An important feature of this invention is that the alteration of the sequence of the inactivated gene of interest must be sufficient in order to avoid reversion. Consequently, a preferred embodiment of the inactivated gene of the present invention is that it is interrupted by an exogenous polynucleotide.

In a specific embodiment of the present invention, the exogenous polynucleotide comprises an antibiotic resistance gene that is used in a pre-selection step in the selection protocol used to obtain the recombinant attenuated strains. In another embodiment, the exogenous polynucleotide sequence used to interrupt the gene of interest comprises a gene coding for an antigenic protein heterologous with respect to the mycobacterium stain to be transfected. In another specific embodiment of this invention, the recombinant mycobacteria of the invention are transformed with an expression vector carrying a polynucleotide encoding an antigenic peptide (i.e., a polynucleotide encoding at least one antigenic epitope) which is heterologous with respect to the strain to be transfected. A preferred recombinant vector is, for example, a vector of the PAL 5000 family. These embodiments may be particularly useful in the design of new vaccines against unrelated pathogens. Illustrative embodiments of antigenic peptide or protein encoding sequences are described below.

Illustrative embodiments of the heterologous antigenic protein to be expressed by recombinant mycobacteria of the present invention include:

1) the nucleotide sequence coding for the whole desaturase antigen of *M. tuberculosis* or at least an antigenic portion of the desaturase antigen. (For example, desaturase derived nucleotide sequence may be inserted in the *M. bovis* BCG stain as a fusion sequence with the gene of interest that codes for a protein involved in the biosynthesis of the purine or pyrimidine bases. This represents an improvement to the conventionally used BCG strains as such recombinant strains will be able to express immunogenic determinants that are specific of *M. tuberculosis*. Such strains should provide improved means to make efficient vaccine preparations.);
2) the 45/47 kD immunogenic protein from *M. tuberculosis* described in PCT application number PCT/FR 96/0166;
3) the surface antigen from the Hepatitis B virus (HBsAg) described in the French patent application number FR 7921811;
4) the nucleotide sequences coding for all or part of HIV glycoproteins, e.g., the genome sequences from HIV-1 described in patent applications GB 8324800, EP 84401834 or EP 85905513 and the genome sequences for HIV-2 described in the patent application EP 87400151;
5) the nucleotide sequences coding for the 65 kD antigen of *M. tuberculosis* (Huygen et al., 1996); and
6) the nucleotide sequence coding for human tumor antigens, such as MAGE antigen, and specifically MAGE-3 antigen, such as described in the U.S. Pat. No. 5,591,430.

It will be appreciated that this invention additionally encompasses immunogenic compositions comprising recombinant mycobacterium strains described above. The invention also encompasses a vaccine composition containing a recombinant mycobacterium according to this invention in combination with a pharmaceutically compatible excipient The present invention also pertains to a vaccine composition for immunizing humans and mammals against a pathogenic strain of mycobacteria, comprising an immunogenic composition as described above in combination with a pharmaceutically compatible excipient (such as, for example, saline buffer), and optionally in combination with at least one adjuvant such as aluminum hydroxide or a compound belonging to the muramyl peptide family.

Various methods for achieving adjuvant effect for the vaccine include the use of agents such as aluminum hydroxide or phosphate (alum), commonly used as 0.05 to 0.1 percent solution in phosphate buffered saline, admixture with synthetic polymers of sugars (Carbopol) used as 0.25% solution. Another suitable adjuvant compounds consist in DDA (dimethyldioctadecyl-ammonium bromide), as well as immune modulating substances, such as lymphokines (e.g., IFN-gamma, IL-1, IL-2 and IL-12) or IFN-gamma inducers compounds, such as poly I:C.

The vaccine composition according to the present invention is advantageously prepared as an injectable form (either as liquid solution or suspension). However, solid forms suitable for solution in or suspension in, liquid prior injection may also be prepared.

In addition, if desired, the vaccine composition may contain minor amounts of auxiliary substances such as wetting or emulsifying agents, pH buffering agents, or adjuvants which enhance the effectiveness of the vaccines.

The vaccine compositions of the invention are administered in a manner compatible with the dosage formulation, and in such amount as will be therapeutically effective and immunogenic. The quantity to be administered depends on the subject to be treated including, e.g., the capacity of the individual's immune system to induce an immune response.

Suitable dosage ranges are of the order of $10^4$ to $10^6$ cfu (colony forming units) at an attenuated recombinant mycobacteria concentration of about $10^6$ cfu/mg. Most preferably, the effective dose is about $10^5$ cfu.

The dosage of the vaccine will depend on the route of administration and will vary according to the age of the patient to be vaccinated and, to a lesser degree, the size of the person to be vaccinated. Most preferably, the vaccine composition according to the present invention is administered via an intradermal route and in a single boost.

In the case of patients affected with immunological disorders such as, for example, immunodepressed patients, each injected dose preferably contains half the weight quantity of the attenuated mycobacteria contained in a dose for a healthy patient.

In the case of neonates, the dose will be approximately four times less than for an adult, and in the case of young children (4–6 years old), the dose will be approximately half the dose used for an adult healthy patient.

In some instances, it will be necessary to proceed with multiple administrations of the vaccine composition according to the present invention, usually not exceeding six administrations, more usually not exceeding four vaccinations, and preferably one or more, usually at least about three administrations. The administrations will normally be at from two to twelve week intervals, more usually from three to five week intervals. Periodic boosters at intervals of 1–5 years, usually three years, will be desirable to maintain the desired levels of protective immunity.

The invention further encompasses polynucleotides containing all or part of the genome of a mycobacterium strain which is devoid of a wild gene encoding a protein involved in the biosynthesis of a purine or a pyrimidine base.

Representative embodiments of this invention will be described in more detail in the following examples.

EXAMPLE 1

Bacterial Strains and Culture Conditions

E. coli strain DH5α was used in this study for cloning experiments, and was grown on liquid or solid Luria-Bertani (L) medium. M. smegmatis mc²155 (Snapper et al., 1990), M. tuberculosis 103 (isolated from a TB patient) and M. bovis BCG strain Pasteur 11732P were grown on liquid Middlebrook 7H9 medium (Difco) supplemented with 0.2% glycerol and 0.05% Tween, or on solid Middlebrook 7H10 medium (Difco). When required, antibiotics were included at the following concentrations: kanamycin (20 μg/ml) and gentamycin (5 μg/l) for mycobacteria, and gentamycin (20 μg/ml) for E. coli. Where indicated, 10% or 2% sucrose was added for M. smegmatis or bacteria of the M. tuberculosis complex respectively (Pelicic et al., FEMS Microbiol Lett. 1996; Pelicic et al., J. Bacteriol. 1996).

Purine auxotrophs were identified by their inability to grow on Sauton medium, unless the medium was supplemented with hypoxanthin (20 μg/ml). Briefly, single colonies were picked and resuspended in 96-well microliter plates containing Sauton medium with or without hypoxanthin supplement. The plates were incubated at 37° C. under 5% $CO_2$. Growth was estimated by following the opacity in adjacent wells with and without hypoxanthin addition.

Electrotransformation

Electrocompetent cells were prepared as previously described (Pelicic et al., Mol. Microbiol. 1996) with minor modifications. M. tuberculosis and M. bovis BCG were grown in 200 ml of 7H9 medium to an $OD_{600}$ of 0.4. Cells were washed three times in 10% glycerol and resuspended in 1 ml 10% glycerol. Aliquots (100 μl) of freshly prepared competent cells were electroporated in the presence of 1 μg of vector DNA in 0.2 cm cuvettes (Biorad) with a single pulse (2.5 kV; 25 pF; 200 ohms). Five ml of fresh medium was then added and the culture was incubated at 32° C. for 24 hours before plating, to allow antibiotic resistance expression. Transfomants were scored after 7–8 weeks of incubation at 32° C.

DNA Extraction and Southern Analysis

Mycobacterial genomic DNA was isolated as previously described (Pelicic et al., Mol. Microbiol. 1996) with minor modifications. One hundred μl of D-cycloserine (1 mg.ml$^{-1}$) was added to a 10 ml saturated culture which was then incubated overnight at 37° C. Cells were pelleted by centrifugation (15 min, 5000×g). The pellet was resuspended in 250 μl of solution I (25% sucrose; 50 mM Tris—HCl pH 8.0; 50 mM EDTA; 500 μl.ml$^{-1}$ lysozyme) and incubated overnight at 37° C. Two hundred and fifty μl of solution II (100 mM Tris—HCl pH 8.0; 1% SDS; 400 μg.ml$^{-1}$ Proteinase K) was then added and the samples incubated for 4h at 55° C. The lysate was then extracted twice with phenol-chloroform and the DNA was concentrated by ethanol precipitation. Approximately one microgram of genomic DNA was digested overnight with an excess of restriction enzyme (30 U) and the fragments separated by electrophoresis through 0.7% agarose gels. Southern-blotting was carried out in 20×SSPE (150 mM NaCl; 8.8 mM $NaH_2PO_4$; 1 mM EDTA pH 7.4) using Hybond–N+ nylon membranes (Amersham). The Megaprime random-primed labeling kit (Amersham) and 5 μCi of (α-$^{32}$p) dCTP were used to label probes. Nonincorporated label was removed by filtration through a Nick Column (Pharmacia). Prehybridization and hybridization were carried out at 65° C. using RH buffer (Amersham) as recommended by the manufacturer. Serial 15 min washes were performed at 65° C. as follows: two washes with (2×SSPE; SDS 0.1%), one wash with (1×SSPE; SDS 0.1%) and two washes with (0.7×SSPE; SDS 0.1%). BioMax MS X-ray film (Kodak) was exposed for 4h to the blots at –80° C.

Construction of Vectors

The thermosensitive origin of replication of pAL5000, present in ts—SacB delivery vectors, was extracted from pB4D* on a 5 kb BamHI (whole pAL5000) or a 3.7 kb EcoRV+KpnI (minimal origin of replication) fragment (Guilhot et al., 1992). The fragments were blunt-ended and cloned into BamI-cut pJQ200 harboring the SacB gene (Quandt and Hynes, 1993). Both orientations were obtained for the 3.7 kb "short" insert (pPR23-1 and pPR23-2) and only one orientation for the 5 kb insert (pPR27).

Plasmids pPR23 and pPR27 were deposited under the provisions of the Budapest Treaty at the National Collection of Cultures of Microorganisms (C.N.C.M.) in Paris on Jun. 19, 1996 and assigned reference Nos. I-1726 and I-1730, respectively.

The purC gene was excised from pMJ1 (Jackson et al., 1996) on a 2.5 kb BamHI fragment and inserted into BamHI-cut pACYC184. The resulting vector was named pMJ100. The aph cassette from pUC4K conferring kanamycin resistance, present on a 1.2 kb PstI fragment, was cloned into pMJ100 at the single PstI site present in purC. PurC::Km was extracted from the resulting pMJ101 vector on a 3.7 kb BamHI fragment, blunt-ended and ligated into BamHI-cut pXYL4, an E. coli vector containing xylE bracketed by two BamHI sites. The resulting vector was named pMJ102. p27CKX, the construct used for the allelic exchange, was obtained by transferring a 4.7 kb BamHI fragment from pMJ102, containing purC::Km and xylE, into BamHI-cut pPR27.

Multiplication and Persistence of *M. bovis*-bcg and *M. tuberculosis* in Various Organs of Mice Infections 30 female C57BL6 mice (assay of *M. tuberculosis*) or Balb/c mice (assay for *M. bovis* BCG) were infected with the wild bacteria (Mt103 or Pasteur strain BCG 1173P2) and 30 mice were infected with the corresponding auxotrophic strain MYC 1551 or MYC 1552. (Recombinant mycobacterium strains MYC 1551 and MYC 1552 were deposited under the provisions of the Budapest Treaty at the National Collection of Cultures of Microorganisms (C.N.C.M.) in Paris on May 12, 1997 and assigned reference Nos. I-1871 and I-1872, respectively.)

Mice were infected via an i.v. route with $10^5$ cfu of Mt103 or MYC 1551 or with $10^6$ cfu of BCG 1173P2 or MYC 1552 that were resuspended in 0.5 ml of PBS buffer supplemented with 0.01% tween.

Multiplication assay

The numeration of colony forming units was performed in the three following target organs: spleen, liver and lung.

The assay was performed at days 1, 7, 14, 21, 42 post-infection with *M. tuberculosis* and at days 1, 7, 14, 28, 42 and 70 post-infection with BCG. For each measurement and each strain, 5 mice were used.

Measurement of the cfu numbers in organs

Organs were recovered and torn to pieces between two glass slides for spleen and lungs or cut then ground with a Stomacher apparatus (2 min. at maximum speed) for the livers. The ground organs were then resuspended in 10 ml solution I (Sauton diluted to ¼ in sterile water then buffered to pH 7.5+OADC (Bacto Middlebrook OADC enrichment Difco) 2%+(gentamycin 10 µg/ml). Various dilutions (1, $10^{-1}$, $10^{-2}$, $10^{-3}$, $10^{-4}$) of these preparations were prepared in solution II (Sauton diluted to ¼ in sterile water and then buffered at pH 7.5) and spread on Petri dishes 7H11 for the wild strains or (7H11+hypoxanthin (20 µg/ml)) or (7H11+ hypoxanthin (20 µg/ml)+kanamycin (20 µg/ml)) for the strains MYC 1551 and MYC 1552 in order to evaluate the number of cfu per organ.

Infection Protocol or Macrophages by the Strains Mt103, BCG 1173P2, MYC1551 and MYC1552

Preparation of Balb/C mice bone marrow macrophages

A 6–8 week old female Balb/C mouse was killed and the femurs were recovered. Bone marrow was extracted from the femurs by repeated passages of a HBSS solution (Gibco BRL) in the medulla channel with a syringe. Once large particles were sedimented, bone marrow cells were recovered by centrifugation (1300 rpm during 5 min) and resuspended in MEM modified Dulbecco culture medium (Gibco BRL)+10% fetal calf serum+glutamine+10% L cells supernatant culture medium (containing growth factors for macrophages).

Then $5\times10^4$ macrophages/well were plated in Lab Tec slides (8 wells) in a volume of 400 µl.

Macrophages infection by the bacteria 8 to 10 days post-isolation

Macrophages in each well of the Lab Tec slides were counted. Bacteria were thawed (1 ml), washed twice in macrophage culture medium and then briefly sonicated in order to disperse them (Ultra-sonicater bath Braun 2200 during 15 sec). The bacterial preparations were then put to sediment during 10 min. About 500 µl of the resultant supernatant medium were used to perform the infection assays. Various dilutions of this supernatant medium were spread on Petri dishes 7H10 in order to evaluate precisely the cfu number that are used to infect macrophages.

The macrophages were then infected with the wild bacteria and the recombinant bacteria. The multiplicity of infection (MOI) is from 0.2 to 1 (i.e., $5\times10^4$ bacteria per well). The infection was maintained during 18h.

Count of the bacteria

The cfu counts perwell was performed at time t=18h, day 4, day 8, day 15. At t=18h: the infection was stopped by three washings of the Lab Tec slides in a HBSS medium (removing of the non-internalized bacteria). At each subsequent time interval, a count of the cfu in each well was performed (four wells/bacterial strain/time point) : macrophages were lysed in a 100 µl lysis buffer volume and various dilutions of this solution were spread for counting the cfu on Petri dishes 7H10 for the wild strains or (7H10+hypoxantbin 20 µg/ml+kanamycin 20 µg/ml) for the strains MYC1551 and MYC1552.

For each time point, a Kinyoun straining was performed on the infected slides, in parallel with the cfu counts, in order to evaluate the macrophage state and to assess in eventual cell lysis.

Figure 2:
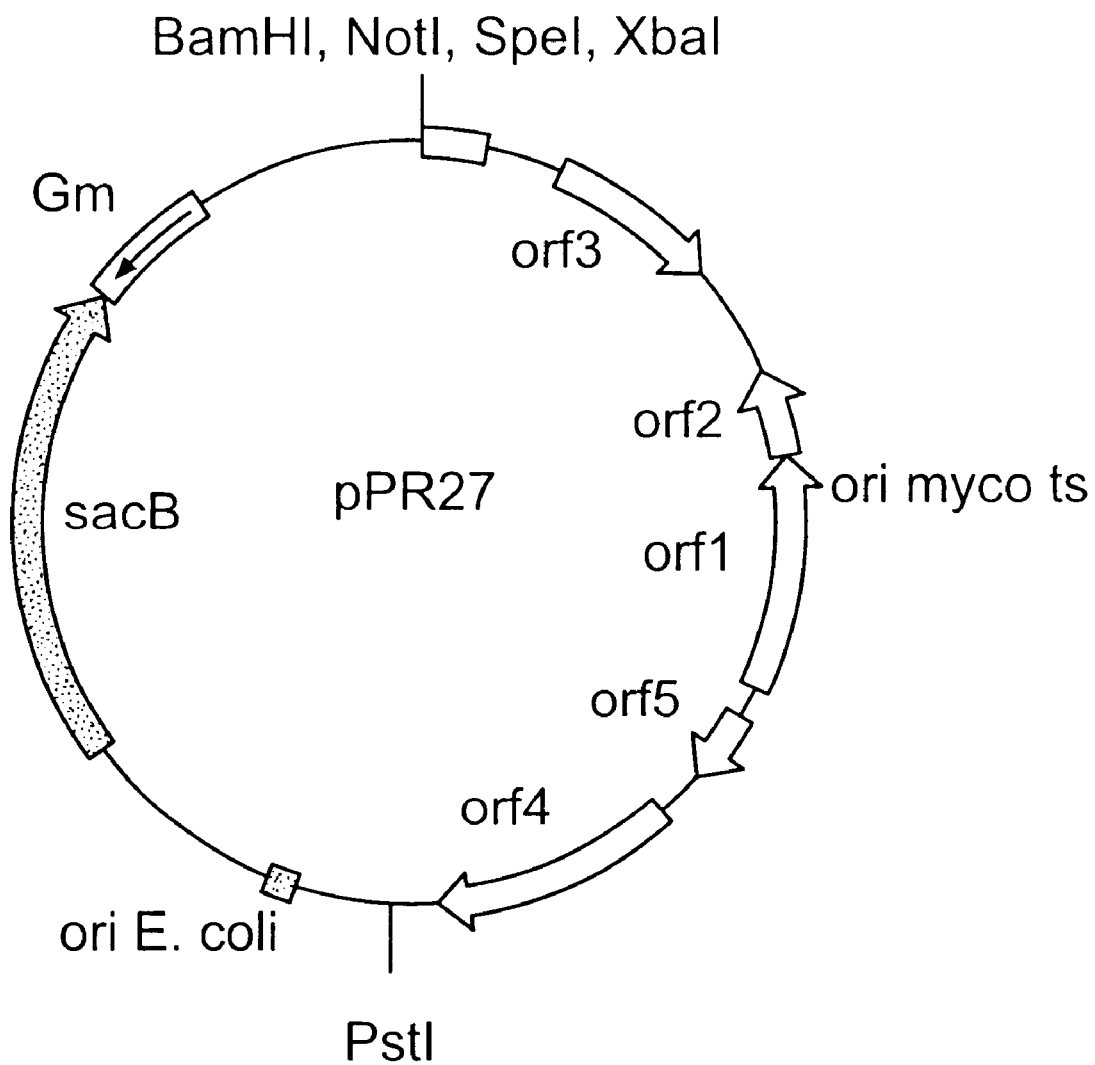
FIG. 2 depicts the design of new vectors for positive selection of rare genetic events (pPR27 is shown as an example). Only single restriction sites which can be used for the subsequent cloning of a transposon or a mutant allele are shown.

Design and Testing of a Novel Methodology for the Selection of Insertional Mutants Recently, it was demonstrated that expression of the SacB gene from *B. subtilis* is lethal to mycobacteria in the presence of sucrose. SacB can therefore be used as a counter-selectable marker (Pelicic et al., *FEMS Microbiol. Lett.* 1996; Pelicic et al., *J. Bacteriol.* 1996; Pelicic et al., *Mol. Microbiol.* 1996). As described above, whether SacB could be used for the positive selection of insertional mutants was tested. A series of conditionally replicative vectors, combining the counter-selective properties of the SacB gene and a mycobacterial thermosensitive origin of replication were constructed (FIG. 2). These ts—SacB vectors were introduced into *M. smegmatis* mc$^2$155 by electroporation (Snapper et al, 1990). *M. smegmatis* transformants, selected at 32° C. on 7H10-gentamycin, were grown in 7H9 at 32° C. until saturation. The efficiency of the different counter-selections were then estimated by plating 100 µl samples of these cultures at different temperatures on 7H10-gentamycin plates with or without 10% sucrose, and counting colony-forming units (CFU). Stability of the pAL5000 thermosensitive origin of replication was measured by plating samples at 39° C., the restrictive temperature for replication, without sucrose addition. The efficiency of SacB counter-selection was estimated by plating samples at 32° C. in the presence of 10% sucrose. By plating on sucrose plates at 39° C., the global counter-selection was assessed (Table 1). Each of the counter-selective pressures, sucrose and growth temperature, was individually low and led to only a limited loss of the vector. However, when transformants were counter-selected for both SacB and the thermosensitive origin of replication, the efficiency of counter-selection was extremely high (Table 1).

TABLE 1

Effect of sucrose and temperature on growth of *M. smegmatis* transformed with pPR27.[a]

| Growth conditions | CFU per 100 µl | Counter-selection efficiency |
|---|---|---|
| 32° C. | $1.2 \times 10^7$ | — |
| 39° C. | 5000 | $4.2 \times 10^{-4}$ |

TABLE 1-continued

Effect of sucrose and temperature on growth of M. smegmatis transformed with pPR27.[a]

| Growth conditions | CFU per 100 µl | Counter-selection efficiency |
|---|---|---|
| sucrose at 32° C. | 3000 | $2.5 \times 10^{-4}$ |
| sucrose at 39° C. | 6 | $5 \times 10^{-7}$ |

[a]Identical results were obtained for pPR23 (data not shown).

The results suggested that ts—SacB vectors could be used to deliver a transposon or a mutated allele into the chromosome of M. tuberculosis, allowing the construction of insertional mutant libraries or gene exchange mutants respectively. This protocol of selection was used for all subsequent mutagenesis experiments. Because trasformants were grown under permissive conditions, problems due to low transformation efficiencies were avoided. During this step of replication, mutants arising by allelic exchange or trasposition can accumulate, overcoming problems due to low frequencies of allelic exchange and transposition. Finally, the great majority of the clones that still contain the vector were eliminated, strongly increasing the proportion of mutants among the survivors.

Gene Exchange Mutagenesis of the purC Gene of M. tuberculosis

The selection protocol used for M. tuberculosis transposon mutagenesis also seemed attractive for the positive selection of gene exchange mutants. Currently, none of the previously described strategies appears suitable for mutagenesis of every gene in M. tuberculosis complex strains (Norman et a;., 1995; Balasubramamian et al., 1996; Pelicic et al., FEMS Microbiol. Lett. 1996). The systems available are very dependent on the target gene, and have proved far less efficient for several "refractory" genes such as purC, which has previously failed to mutagenize in M. tuberculosis (unpublished data). Because M. tuberculosis purine auxotrophic mutants may have a vaccinal potential (Fields et al., 1986), the purC gene from the purine biosynthetic pathway was a perfect candidate for testing this new tool (Jackson et al., 1996). A mutated allele, purC::Km, was inserted into pPR27 along with xylE as a reporter gene. Since the gentamycin resistance gene is not a reliable marker in M. tuberculosis, this reporter activity could facilitate the screening by discriminating possible allelic exchange mutants which have lost the xylE gene from SacB mutants with the whole vector integrated into the chromosome and which are thus phenotypically xylE[+]. Indeed, xylE expression in mycobacteria can easily be tested by spraying colonies on plates with a solution of catechol and observing a bright yellow coloration (Curcic et al., 1994).

Figure 3:
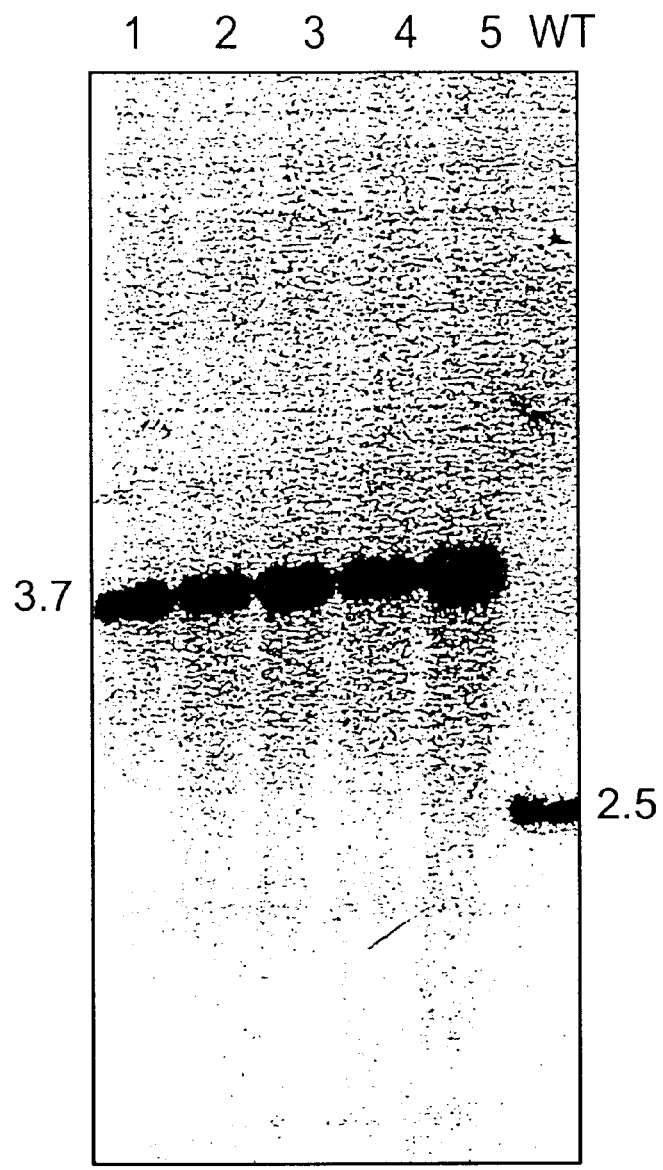
FIG. 3 depicts a Southern-blot analysis of *M. tuberculosis* purC mutants and the expected schematic pattern of hybridization for an allelic exchange mutant. Five auxotrophic mutants were picked at random (clones 1 to 5). Chromosomal DNA was digested with BamHI and probed for hybridization with the p27CKX vector. *M. tuberculosis* DNA was included as a control (WT). Molecular weights are indicated in kb.
Figure 3:
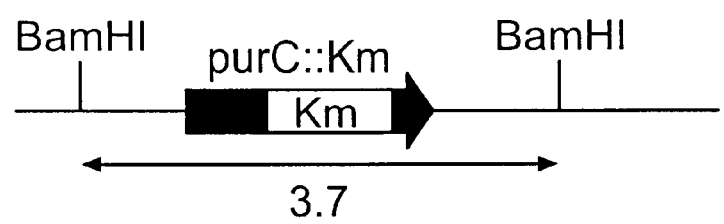

Plasmid p27CKX was introduced in M. tuberculosis by electroporation and transformants were selected at 32° C. on 7H10-kanamycin. Several transformants were grown in liquid culture supplemented with hypoxanthin, a purine precursor. The culture was then plated at 39° C. on 7H10-kanamycin+2% sucrose+hypoxanthin plates. With an initial inoculum of $10^7$ colonies, 200 transformants were obtained on counter-selective plates. All presented the expected phenotype for allelic exchange mutants: Suc[r], Km[r], XylE[−]. The phenotypic analysis confirmed that they were purine auxotrophs, as they were not able to grow on Sauton medium, a synthetic medium containing no purine bases, without the addition of hypoxanthin. To unambiguously confirm that the selected clones were allelic exchange mutants, several colonies were grown m 7H9 supplemented with hypoxanthin. Genomic DNA was extracted and analyzed by Southern-blotting using the purC gene as a probe (FIG. 3). M. tuberculosis 103 DNA which was included as a control (WT), showed one hybridizing fragment of 2.5 kb. As expected for allelic exchange mutants, all the clones presented a single hybridizing fragment approximately 1.2 kb longer than that in the wild-type strain (FIG. 3). This 1.2 kb-increase corresponded to the size of the kanamycin resistance cassette which was inserted into the mutated allele. Therefore, all the tested transformants, selected on counter-selective plates, were indeed allelic exchange mutants. This confirmed that ts—SacB delivery vectors, in addition to being useful for transposon mutagenesis, are also highly efficient for gene exchange mutagenesis.

Figure 4:
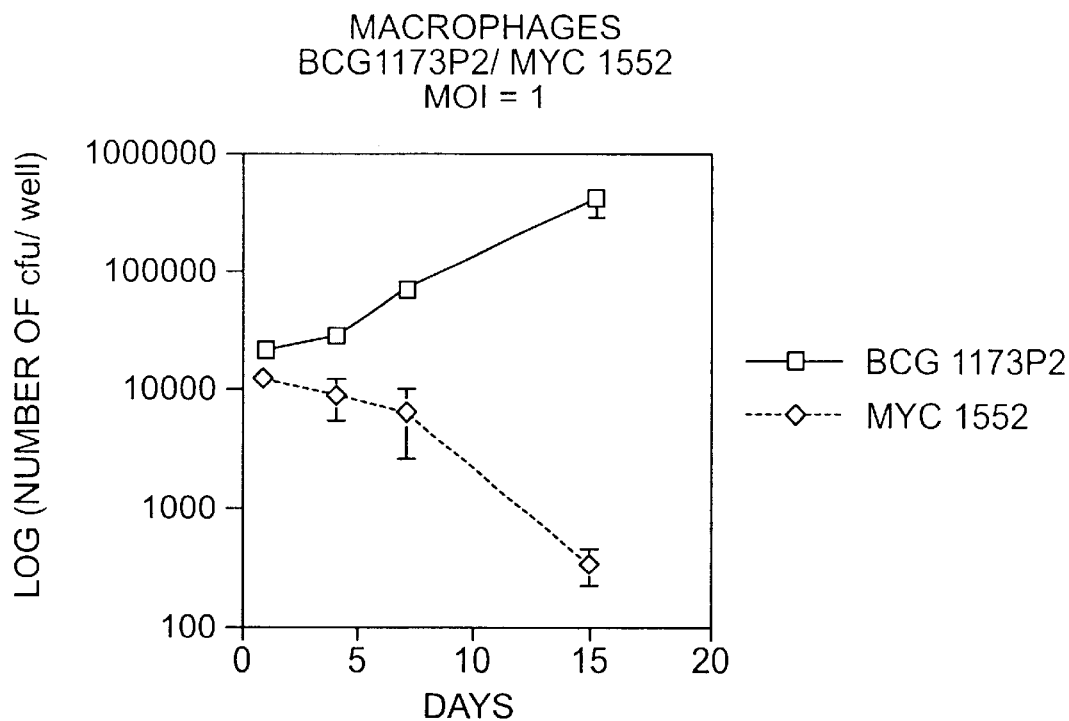
FIG. 4 depicts the number of colony forming units found in macrophages infected in vitro with either wild type *M. bovis* BCG (Pasteur strain 1173P2) (-□-) or the corresponding recombinant mutant strain MYC 1552 ( . . . ◊ . . . ).
Figure 5:
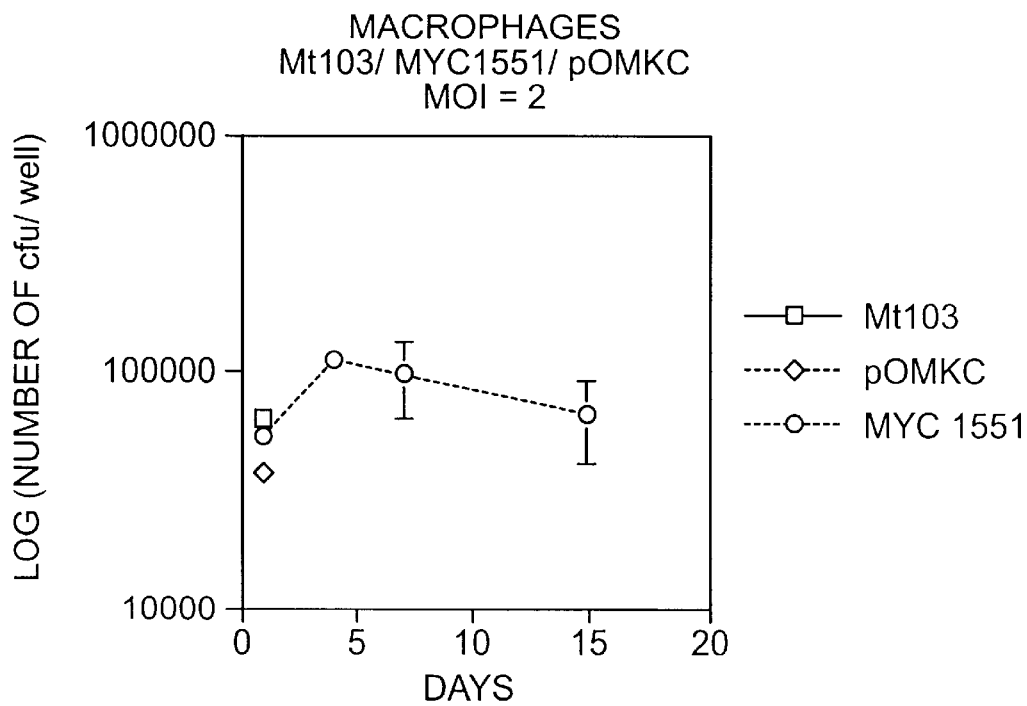
FIG. 5 depicts the number of colony forming units found in macrophages infected in vitro with wild type *M. tuberculosis* Mt103 (-□-), the corresponding recombinant mutant strain, MYC 1551 ( . . . ○ . . . ) and the recombinant mutant strain complemented with vector carrying the purC gene ( . . . ◊ . . . ). These results demonstrate that the MYC-1551 strain is not replicating due to the absence of a functioning purC gene.
Figure 6A:
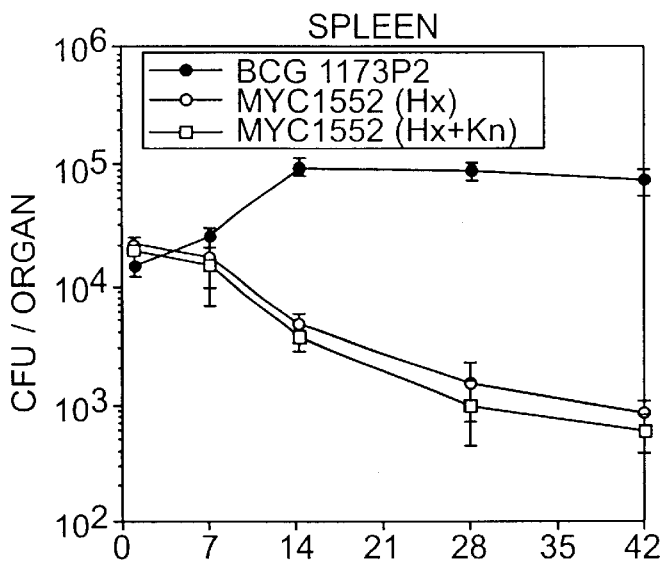
FIG. 6 depicts the number of colony forming units found in various organs of mice infected in vivo with wild type *M. bovis* BCG (Pasteur strain 1173P2) ( . . . ● . . . ), recombinant mutant strain MYC 1552 plated and cultivated (after sacrifice of the infected animal) in hypoxanthin ( . . . ○ . . . ) and recombinant mutant strain MYC 1552 plated and cultivated in hypoxanthin and kanamycin (-□-). These results demonstrate that the mutant strain is maintained in the infected organ but is not replicating.
Figure 6B:
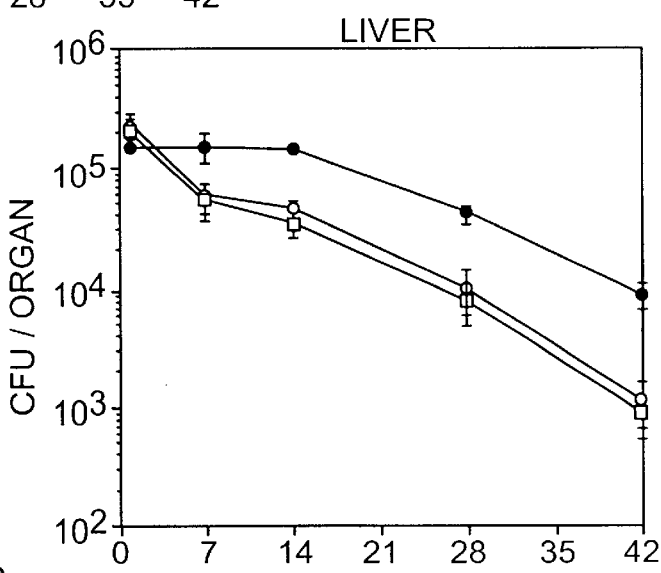
Figure 6C:
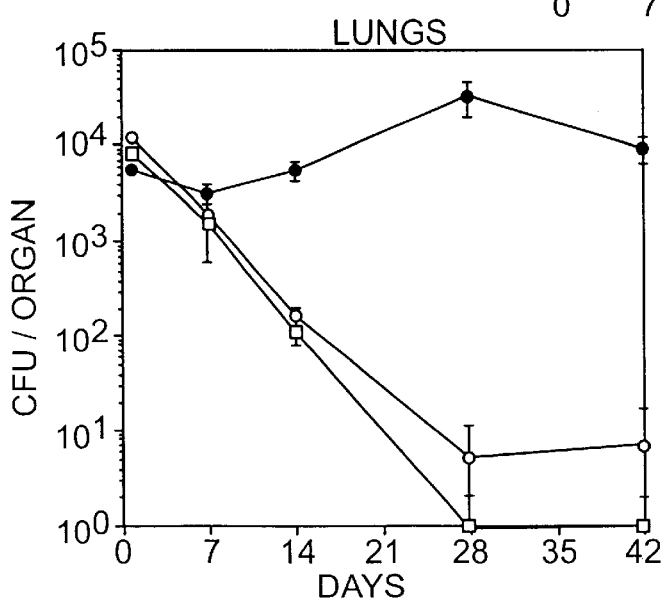

In vitro and in vivo Infection with the Wild Strains and the Recombinant Strains 1) In mice bone marrow macrophages In contrast with the wild type Mt103 and BCG 1173P2 which multiplied inside macrophages between 0 and 15 days, (the wild type M. tuberculosis lysed the macrophages before 4 days, which explains the cfu counts were only performed at 18h) the auxotrophic strains of M. tuberculosis MYC1551 and of BCG MYC 1552 did not multiply within the same period of time. MYC 1552 was progressively eliminated from macrophages (FIG. 4). MYC1551 seemed to persist in the macrophages without multiplying as the number of cfu's recovered at day 15 was almost the same as at 18h (FIG. 5). Moreover, the strain identified as pOMKC corresponding to MYC1551 complemented with the wild type copy of the purC gene carried on a plasmid, behaved like the wild type Mt103. This result confirmed that the attenuation of MYC1551 is due to the inactivation of the purC gene and not to a polar effect of the mutation carried by this gene on adjacent genes.

2) In mice

Figure 7A:
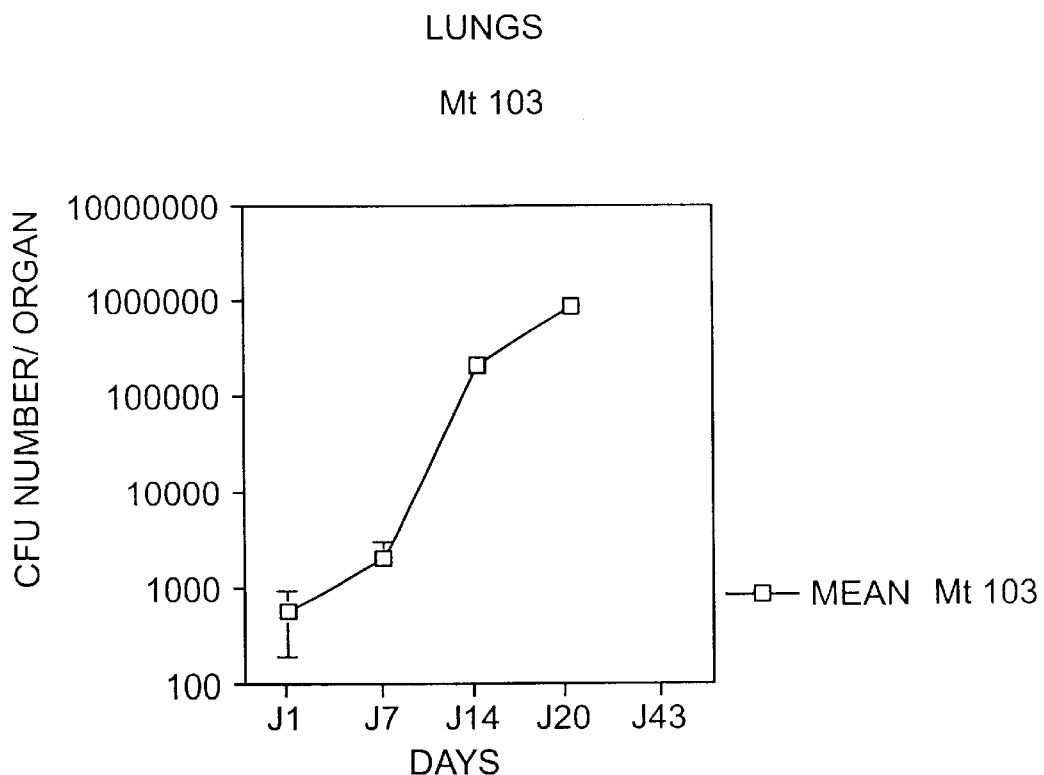
FIG. 7 depicts the number of colony forming units found in the lungs of mice infected in vivo with wild type *M. tuberculosis* Mt103 (FIG. 7A) and with the corresponding recombinant mutant strain, MYC 1551 (FIG. 7B).
Figure 7B:
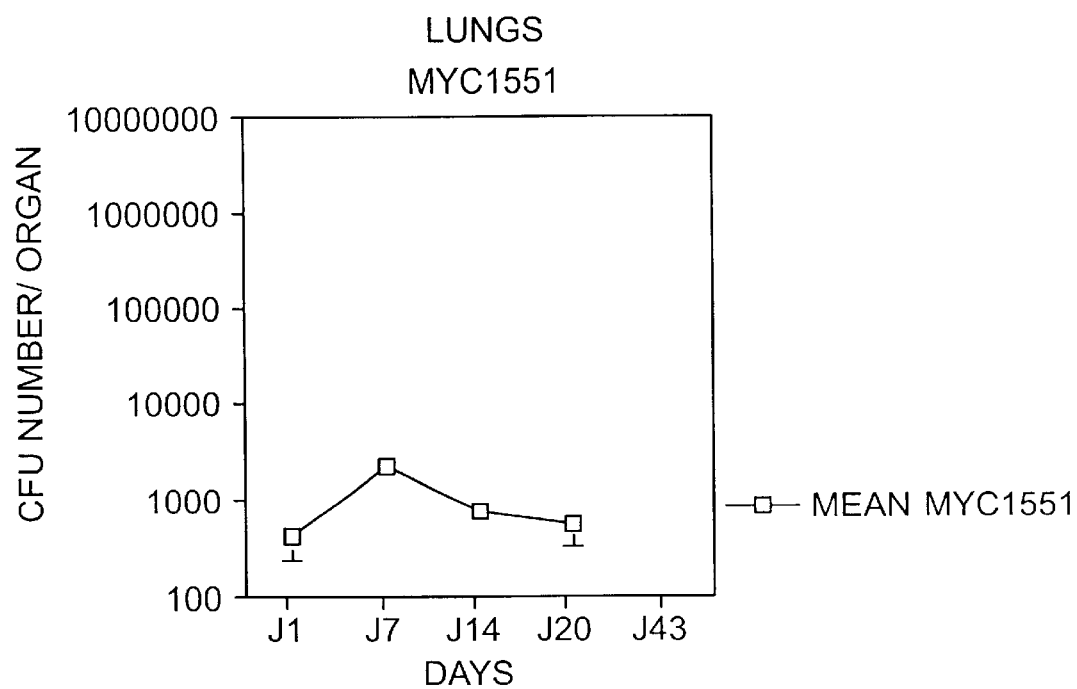
Figure 8A:
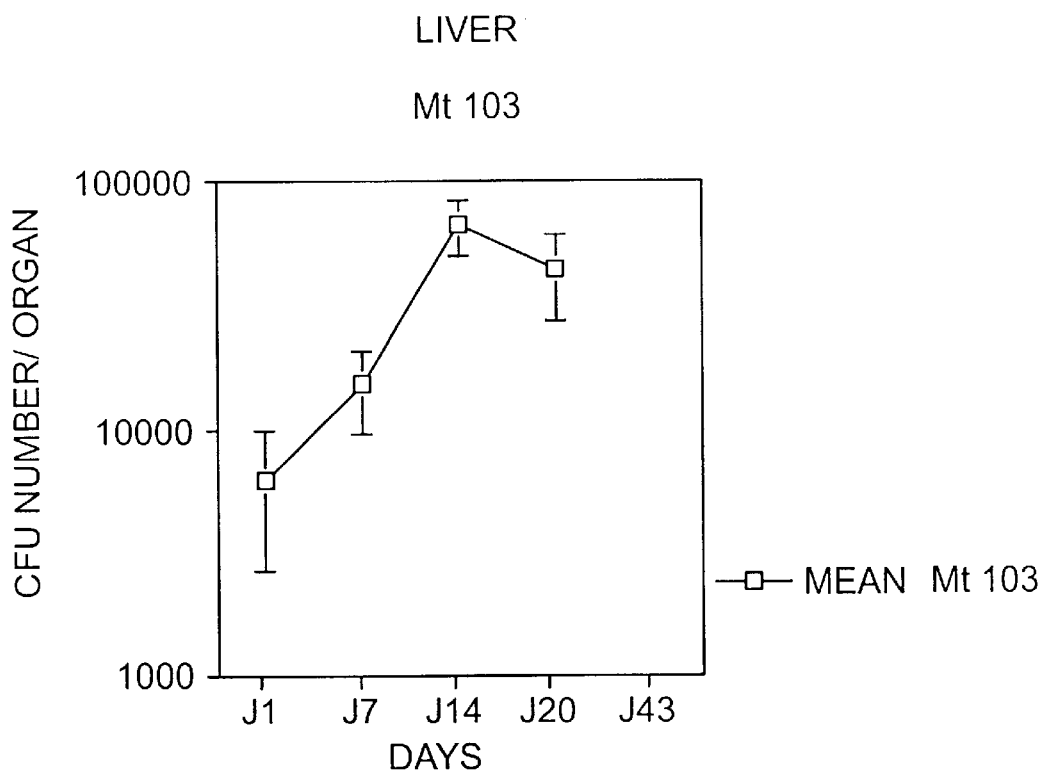
FIG. 8 depicts the number of colony forming units found in the liver of mice infected in vivo with wild type *M. tuberculosis* Mt103 (FIG. 8A) and with the corresponding recombinant mutant strain, MYC 1551 (FIG. 8B).
Figure 8B:
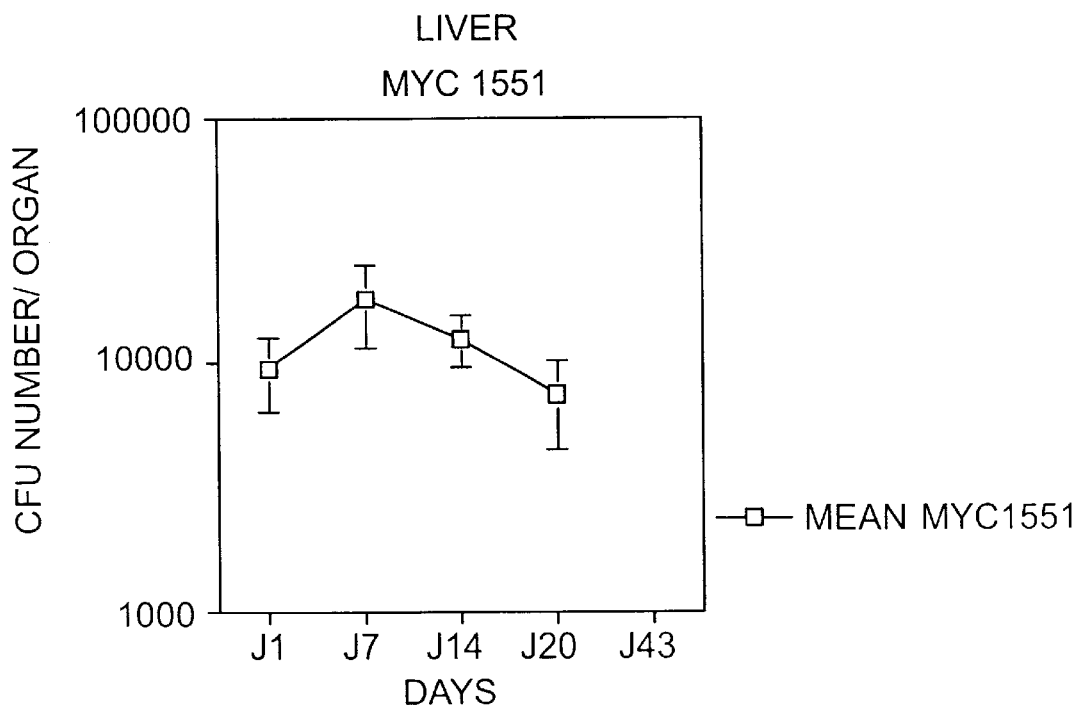
Figure 9A:
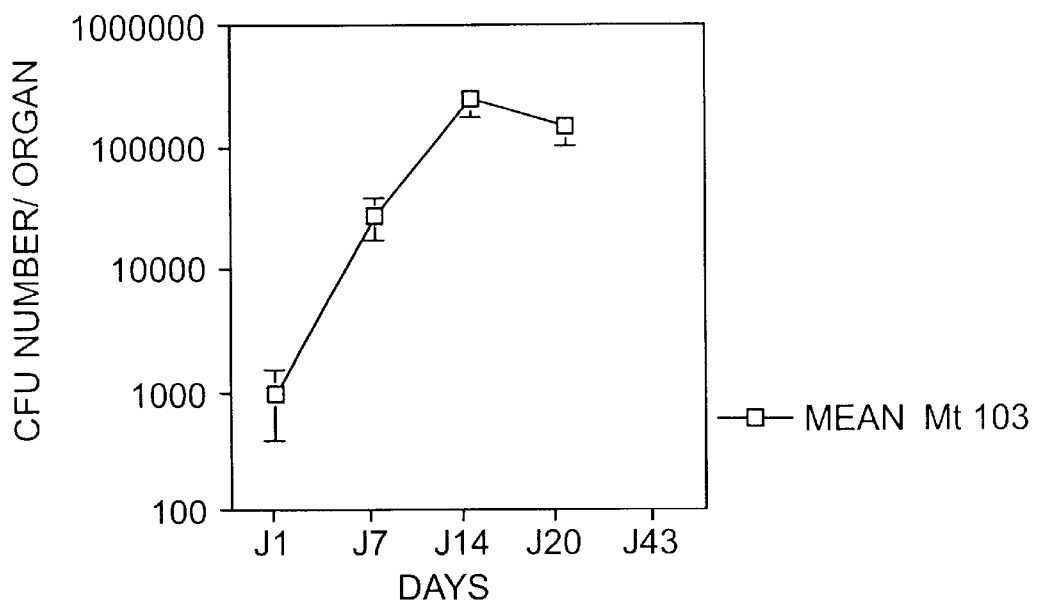
FIG. 9 depicts the number of colony forming units found in the spleen of mice infected in vivo with wild type *M.* tuberculosis Mt103 (FIG. 9A) and with the corresponding recombinant mutant strain, MYC 1551 (FIG. 9B).
Figure 9B:
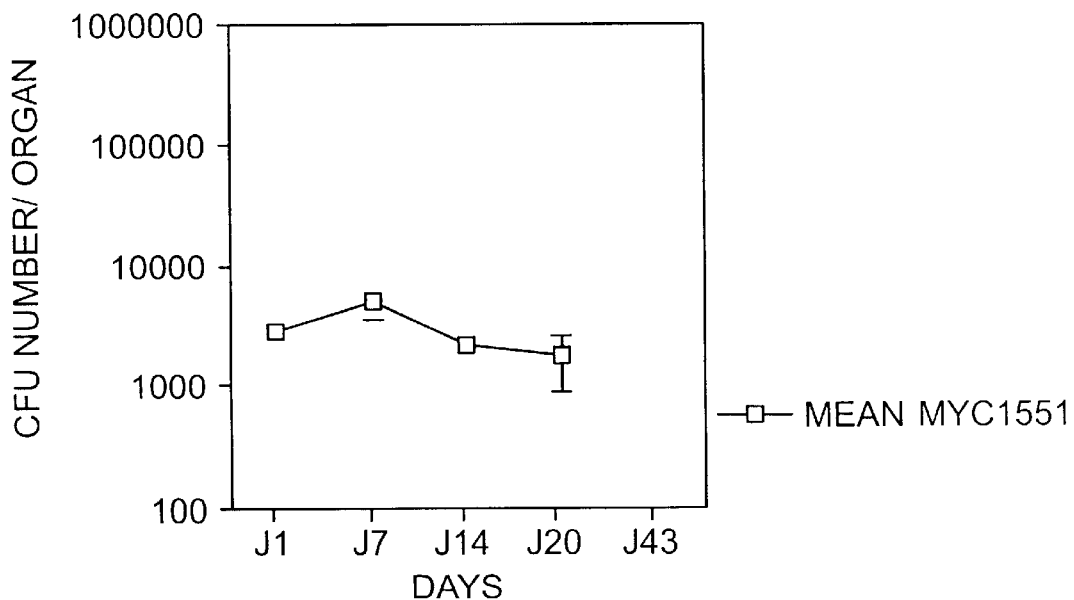

As shown in FIGS. 7–9, strains MYC1551 and MYC1552 were attenuated as compared to the wild type strains Mt103 and BCG 1173P2. MYC1552 did not multiply at all (not even between day 1 and day 15) and was progressively eliminated from all organs. These results confirm what was observed in macrophages (FIG. 4). MYC1551 did not multiply on the overall period between day 1 and day 20. Nevertheless, this strain seemed to persist in all organs during the same period of time. These results also confirm what was observed in macrophages (FIG. 5).

EXAMPLE 2

Bacterial Strains and Culture Conditions

Escherichia coli XL1-Blue was used for cloning experiments and grown on liquid or solid Luria-Bertani medium. The mycobacterial strains, M. bovis BCG strain Pasteur 1173P2, M. tuberculosis MT103 (isolated from a TB patient) and H37Rv (ATCC 27294) were grown on liquid Middlebrook 7H9 medium (Difco) supplemented with 0.05% Tween 80 or on solid Middlebrook 7H10 or 7H11 medium (Difco). When required, kanamycin (20 µg/ml), gentamycin (10 µg/ml) or hypoxanthin (20 µg/ml), a purine precursor, were added to the growth media. M. tuberculosis H37Rv was obtained from the American Type Culture Collection, Rockville, Md., and stored as a single-cell suspension at −70° C. (Grover et al., 1967).

Plasmid Construction

Plasmid pMJ104 was constructed by inserting the 3.7 kb BamBI fragment containing purC::Km from pMJ101 into the BamHI site of pJQ200 (Pelicic et al., 1997). This plasmid is unable to replicate in mycobacteria. The plasmid pMJ105 was created by excising the 1090 bp EcoRV—HincII fragment from plasmid pMJ1, harbouring the purC gene flanked by 120 bp upstream and 80 bp downstream, and by cloning it into plasmid pOMK (Jackson et al., 1996). pMJ105 is able to replicate in mycobacteria.

Experimental Animals

For these experiments, C57BL/6j or BALB/c female mice 6 to 8 weeks old (purchased from CERJ, Le Genest St Isle, France) were utilized. They were kept under good conventional housing conditions for up to 3 months. Mice inoculated with *M. tuberculosis* strains were maintained in biohazard facilities and housed in cages contained within a safety enclosure. Forty-seven male and female outbread Hartley-stin guinea pigs (Charles River Laboratories, Inc. Wilmington, Mass., USA) were utilized in this study. They were individually housed in polycarbonate cages with stainless steel grid floors and feeders and were provided with commercial guinea pig chow and tap water ad libitum. Each animal was randomly assigned a vaccine group and sacrifice interval. Prior to vaccination with the purC auxotrophic strain of *M. tuberculosis* and/or challenge with virulent *M. tuberculosis*, the animals were moved into a BL3 biohazard suite and kept in individual stainless steel cages with grid floors and water bottles.

Preparation and Infection of Mouse Bone Marrow Macrophages

Bone marrow cells were flushed from the femurs of 7 to 8 weeks-old BALB/c mice and suspended in Dulbecco medium with low glucose (1 g/liter) and high carbonate (3.7 g/liter) concentrations (Gibco BRL) and enriched with 10% heat-inactivated foetal calf serum (Dominique Dutscher), 10% L-cell conditioned medium and 2 mM glutamine. For the infection assays, mouse bone marrow macrophages were seeded in 8-wells Lab-Tek chamber slides (Nalgen Nunc International) ($5 \times 10^4$ cells/well in a volume of 400 µl) and allowed to differentiate for 6 to 8 days. An aliquot of the *M. tuberculosis* suspensions used to infect macrophages was plated onto Middlebrook 7H10 agar to establish the exact number of bacteria in the inoculum. Prior to macrophage infection, mycobacteria were washed twice in the cell culture medium described above, and sonicated in a sonicator bath (Branson 2200) for 15 seconds. Bacterial aggregates were allowed to sediment for 10 minutes. The top 500 µl were recovered and bacterial concentrations were adjusted to $2 \times 10^4$ bacteria/ml with cell culture medium. The infection assay was as follows. The culture medium of each Lab-Tek chamber slide well was removed and replenished with 500 µl of the mycobacterial suspension described above in order to have a multiplicity of infection (MOI) of 1:1. Control wells containing non-infected macrophages received 500 µl fresh culture medium. Infected and non-infected cultures were incubated at 37° C. in a 5% $CO_2$ atmosphere for 18 hours. After 18 hours, infection was terminated by removing the overlaying medium and washing each well three times with 500 µl Hank's buffered salt solution (HBSS) (Gibco BRL) before adding 400 µl of fresh culture medium per well. At day 1 (18 h), 4, 7 and 11, the number of intracellular colony forming units (CFU) was evaluated. For this, macrophages monolayers were washed three times in HBSS buffer and then lysed in 100 µl of cell culture lysis reagent (Promega). Different dilutions of this lysis solution were plated onto 7H 10 or 7H 10 supplemented with hypoxanthin plates to perform the mycobacterial colony counts. At each time point, a Lab-Tek chamber slide containing infected macrophages and cultivated in the same conditions was subjected to staining for acid-fast bacilli in order to check the macrophages viability. This infection experiment was carried out in duplicate.

Mycobacterial Multiplication in Mice

Mice were infected intravenously either with either $10^5$ cfu of MYC1551 and MT103 or $10^7$ cfu of MYC1552 and BCG in 0.5 ml of phosphate saline buffer. At every time point, mice were euthanized with $CO_2$, the spleen, lung and liver were removed aseptically and homogenized either manually using two glass slides for the spleen and lung or using a Stomacher 80 (Seward) homogenizer for the liver. Homogenates were resuspended in 10 ml of buffer (Sauton 25% supplemented with 2% Middlebrook OADC (Difco), pH 7.5). For the lung, gentamycin were added at a final concentration of 10 µg/ml to avoid contamination. Enumeration of bacteria in the organs of infected animals was performed by plating 10-fold serial dilutions (performed in Sauton 25%, pH 7.5) of organ homogenates on 7H11 medium (supplemented with hypoxanthin for the auxotroph mutants). Colonies were counted after 3 to 4 weeks of incubation at 37° C. for the wild type strains and after 6 to 8 weeks for the mutants. The data were expressed as the geometric means +/− standard deviation of counts obtained with 5 to 6 mice.

Vaccination, Challenge and Necropsy of Guinea Pigs

Each guinea pig received approximately $10^7$ cfu of either wild type BCG, the corresponding BCG auxotrophic stain MYC1552, or the *M. tuberculosis* auxotrophic mutant MYC1551. A volume of 0.2 ml of vaccine or sterile physiological saline (placebo) was injected subcutaneously into the inguinal region of each animal. Three, six and nine weeks post-vaccination, three animals from each of the three vaccine groups were euthanized with a peritoneal injection of 2 ml of sodium pentobarbital (Sleepaway; Fort Dodge Laboratories, Inc., Ft Dodge, Iowa). One-half of the spleen and the right lower lobe of the lung were aseptically removed and homogenized separately in Teflon-glass homogenizers in 4.5 ml of sterile physiological saline. The number of viable mycobacteria in each organ was determined by inoculating appropriate dilutions onto duplicate 7H10 plates supplemented with hypoxanthin. Data were expressed as mean $log_{10}$ number of viable organisms per tissue. Nine weeks post vaccination, the challenge inoculum of H37Rv was rapidly thawed and diluted just prior to infection. All animals were infected via the respiratory route by use of an aerosol chamber as previously described (Wiegeshaus et al., 1970). The infecting inoculum of viable H37Rv was empirically adjusted to result in the inhalation of 5 to 10 viable organisms per animal. Five weeks post-respiratory challenge, all remaining guinea pigs were euthanized by the intraperitoneal injection of 2 ml of sodium pentobarbital. The abdominal and thoracic cavities were opened aseptically and the spleen and right lower lobe were removed for bacterial culture.

Lymphoproliferation Assay

Mitogen- and antigen-induced lymphoproliferation was assessed in vitro by an established procedure (Bartow and McMurray, 1989). Lymphocytes from the spleen were suspended in complete tissue culture medium and plated in 96 well microtiter plates (Falcon 3072, Becton Dickinson and Company, Franklin Lakes, N.J.) at $2 \times 10^5$ cells per well. Triplicate cultures were stimulated with purified protein derivative (PPD; Statens Seruminstitut, Copenhagen, DK) at concentrations of 25 µg/ml or concanavalin A (Sigma) at a concentration of 10 µg/ml. Control cultures received cells and medium alone. The concacanavalin A (ConA) were used as control as a non-specific inducer of lymphoproliferation. The cultures were incubated for 4 days at 37° C. in a 5% CO2 environment; labeled with 1 µCi of tritiated thymidine per well for the last 6 hours, and harvested. The cellular uptake of thymidine was quantified in a liquid scintillation counter. The result were expressed as mean counts per minute (cpm) of stimulated cultures minus mean cpm of unstimulated cells of the same source. The stimulation index (SI) was calculated by dividing the cpm in stimulated cultures by the cpm from unstimulated cultures of the same animal's cells.

Tuberculin Skin Test

The delayed-type hypersensitivity reaction was evaluated by the intradermal injection of 0.1 ml of PPD containing 100 tuberculin units RT-23, Statens Seruminstitut) on a shaved area of the abdomen. The mean diameter of induration was measured in millimeters and recorded 24 hours later.

Statistical Methods

Analysis of variance was utilized to test the effects of vaccination on tissue bacterial load. When significant treatment effects were indicated, differences between means were assessed by Duncan's multiple range test A 95% confidence level was set for all tests. All analyses were performed using PC SAS 6.12 (SAS Institute, Cary, N.C.).

Construction of purC- Mutants of M. bovis BCG and M. tuberculosis

M. bovis BCG strain 1137P2 was electroporated using 2 μg of plasmid pMJ104. Two $Km^r$ transformant were obtained. Their genomic DNA were extracted and analysed by Southern blot using the purC gene as a probe. One of the two clones exhibited the correct hybridization pattern for an allelic exchange mutant The other one corresponded to the wild type and was probably a $Km^r$ mutant of *M. bovis* BCG. The candidate clone was phenotypically tested. As expected, it required purines or hypoxanthin (a precursor of purine bases) to grow on 7H9 or 7H10. This mutant was renamed MYC1552.

The purC- mutant of *M. tuberculosis* MT103, named MYC1551, was obtained as described in Pelicic et al., 1997. Like MYC1552, MYC1551 is dependent on the presence of purines or hypoxanthin in the medium to multiply.

Evaluation of the Reversion Frequency of MYC1551 and MYC1552

To estimate the stability of the mutation introduced by allelic exchange in *M. bovis* BCG and *M. tuberculosis,* cultures of MYC1551 and MYC1552 grown in 7H9 containing kanamycin were plated on 7H10 with kanamycin and hypoxanthin or 7H10 alone. In all the experiments (repeated independently 4 and 2 times for MYC1552 and MYC1551 respectively), no colony forming unit was detected on 7H10. In contrast, an average of $8.10^7$ cfu/ml and $4.10^8$ cfu/ml were obtained respectively for MYC1551 and MYC1552 on 7H10 supplemented with hypoxanthin and kanamycin. Therefore, the reversion frequency was estimated to be lower than $10^{-8}$ events per cell and per generation. The same experiment was repeated with cultures grown in 7H9 liquid medium without kanamycin and the same results were obtained.

Growth Characteristics of the Purine Auxotrophs in Macrophages

The ability of the purine auxotrophs to persist and multiply within bone-marrow macrophages from C57BL/6 mice was evaluated. $5\times10^4$ macrophages were infected at a multiplicity of infection close to 1 with the parental and the mutant strains. Over a period of 15 days, the infection was followed by counting the viable bacteria (FIGS. 10A and 10B). *M. tuberculosis* MT103 and *M. bovis* BCG 1137P2 multiplied within the macrophage with an apparent doubling time of 36 h and 59 h respectively. At 8 days post-infection, macrophages were packed with *M. tuberculosis* and most of them lysed. With *M. bovis* BCG, the infection was followed for 15 days without apparent lysis of the macrophages. The purine auxotrophs exhibited totally different growth characteristics as compared to their parental strains. In both cases, infections were contained. MYC1551 persisted, but the number of viable bacteria did not increase. MYC1552 was gradually eliminated and after 15 days less than 3% of the inoculum was still viable. These results demonstrate that the disruption of the purC gene alters the ability of *M. tuberculosis* and *M. bovis* BCG to multiply within mouse bone-marrow macrophages.

To confirm that this phenotype was due to the mutation of the purC gene and not to a polar effect of the kan gene insertion, a complementation experiment was performed. Plasmid pMJ105 containing purC was electro-transferred into MYC1551. Transformants no longer required purines to grow in 7H9 or 7H10. MYC1551:pMJ105 was used to infect macrophages (FIG. 10B). As expected, the presence of purC on the plasmid fully restored the ability of MYC1551 to multiply within macrophages.

Persistence of the Auxotrophic Mutants and Their Parental Couterparts in Mice *M. tuberculosis* ($10^5$ cfu) or *M. bovis* BCG ($10^6$ cfu) were used to infect BALB/c mice intravenously. The infection was followed by killing the mice at different time points and counting the number of viable bacteria in the liver, spleen and lung (FIGS. 11 and 12).

For the wild type *M. tuberculosis,* there was a large increase in the number of cfu in the three organs during the first two or three weeks: 2.5 logs in the spleen (day 14), 1 log in the liver (day 14), 3 logs in the lung (day 21). At this time the infection was controlled; the bacillary load was stabilized both in the lung and the spleen at $10^6$ and $10^5$ cfu per organ, respectively. In the liver, the bacterial burden decreased to reach a plateau at $10^4$ cfu. For the purine auxotroph MYC1551, the situation was quite different. The initial multiplication was dramatically reduced with less than half a log of increase in every organ at the peak occurring at day 7. Then, the bacilli were gradually eliminated from the three organs to become undetectable at day 63.

For BCG, the initial multiplication was slower than for *M. tuberculosis:* only half a log of increase in the spleen at day 14 and almost no multiplication in the lung and the liver. From day 14 in both the liver and the spleen and from day 28 in the lung, the number of viable bacilli decreased gradually to reach $5\times10^3$, $10^4$ and $5\times10^4$ in the lung, liver and spleen, respectively, at day 70 when the experiment was stopped. With the BCG auxotroph (MYC1552), the number of bacilli began to decrease immediately after the infection, and no bacteria were recovered from the lung at day 42, or from the liver at day 56. In the spleen, a few colonies were recovered even at day 70 when the experiment was stopped.

These results established that the mutations in the purC gene of both BCG and *M. tuberculosis* attenuated the virulence of these strains in the mouse model. The experiment was repeated in a second susceptible mouse line, C57BL/6, with *M. tuberculosis* MT103 and MYC1551 but without any differences noted. MYC1551 and MYC1552 were eliminated very efficiently to become almost undetectable at the end of the experiment (day 63 for *M. tuberculosis* and day 70 for BCG). However, they persisted for a while since bacteria were recovered from every organ during the first 6 weeks. The main difference in the behaviour of the two purine auxotrophs thus appears in the first week post infection. While MYC1551 increased slightly in every organ tested, MYC1552 began to decline immediately after the infection. After this short lag time, MYC1551 was cleared as efficiently as MYC1552.

Cell-mediated Immune Responses Induced by the Purine Auxotrophs and Protective Efficacy in the Guinea Pig Model In order to evaluate the protective efficacy of the purine auxotrophs, the guinea pig was chosen because it is much more susceptible to *M. tuberculosis* infection than the mouse. Furthermore, BCG protection is easier to demonstrate in the guinea pig. While a maximum of one log difference in the cfu number can be obtained in the lung and spleen of unimmunized as compared to BCG vaccinated mice, differences of one to two logs in the lung and 4 logs in the spleen are often obtained between naive and BCG vaccinated guinea pigs following low-dose aerosol challenge (McMurray, 1994).

Outbred Hartley strain guinea pigs were inoculated subcutaneously with $10^7$ cfu of either BCG 1173P2, MYC1552 or MYC1551. Three animals from each treatment group were euthanized at three, six and nine weeks post infection. The number of viable mycobacteria was determined in one half of the spleen and the right lower lobe of the lung. Three weeks post-infection, 870 cfu+/−651 of BCG 1173P2 were found in the spleens of three guinea pigs. In contrast, 90 cfu were recovered from only one of three guinea pigs infected with MYC1551, and no bacteria were found in any of the animals vaccinated with MYC1552. Six and nine weeks post-infection, no bacillus was recovered from the spleens of any animal of any of the three treatment groups. At no time point, were bacilli recovered from the lungs of any vaccinated animal. These results show that the purine auxotrophs are attenuated even in the highly susceptible guinea pig as well as they were in the mouse model.

The cell mediated immune response induced by the different strains was evaluated by measuring the lymphocyte proliferation induced by PPD, and cutaneous delayed-type hypersensitivity. Nine weeks post-vaccination, all the vaccinated animals exhibited a detectable skin test reaction against tuberculin (Table 2). The mean induration diameters, measured 24 hours following the intradermal injection, were 13.9+/−0.9, 15.5+/−1.0 and 11.1+/−2.2 respectively for the BCG, MYC1552 and MYC1551 infected guinea pigs. The lymphocyte proliferation to PPD was measured for the vaccinated animals euthanized six and nine weeks post vaccination (Table 3). In every case, PPD induced a strong proliferative response which decreased between the sixth and ninth weeks post-immunization. The stimulation indexes ranged from 4.4 to 8.9 at six weeks, and from 2.9 to 6.1 at nine weeks and were not statistically different ($p > 0.05$).

Nine weeks post-vaccination, the remaining animals were infected via the aerosol route with a dose empirically adjusted to result in the inhalation of 5 to 10 viable *M. tuberculosis* I37Rv bacilli per animal. Five weeks later, viable *M. tuberculosis* were recovered quantitatively from the spleen and the lung (Table 4). In the lung, both MYC1551 and MYC1552 exhibited a level of protection comparable with the one obtained with BCG 1173P2, namely 1 log of difference in the cfu count between the vaccinated and unimmunized animals. As expected, vaccine-induced protection was most visible in the spleen. BCG and MYC1551 induced a significant level of protection, while in guinea pigs vaccinated with MYC1552, the number of cfu were comparable to those observed in the unimmunized animals.

The Duncan Multiple Range Test indicated that there was no significant difference in the number of tubercle bacilli recovered from the lung between different groups of vaccinated animals but that the difference between vaccinated and non-vaccinated groups was statistically significant ($p<0.05$). In the spleen, analysis revealed that the difference between BCG and MYC1551 was not significant. However, the number of mycobacteria in the spleens of animals vaccinated with BCG was significantly lower than the number in MYC1552-vaccinated and unimmunized controls.

TABLE 2

Tuberculin skin test on guinea pigs injected via the intradermal route with 100 tuberculin units nine weeks post-infection.

|  | BCG | MYC1552 | MYC1551 | Control |
|---|---|---|---|---|
| induration diameter (mm) | 13.0 | 16.0 | 5.0 | 0 |
|  | 12.5 | 17.0 | 12.0 | 0 |
|  | 17.5 | 13.5 | 18.5 | 0 |
|  | 13.5 |  | 11.0 | 0 |
|  | 13.0 |  | 9.0 | 0 |
| Mean +/− SEM. | 13.9 +/− 0.9 | 15.5 +/− 1.0 | 11.1 +/− 2.2 | 0 |

TABLE 3

Proliferation of lymphocyte from vaccinated guinea pigs to PPD.

| Group | Necropsy | ConA (10 µg/ml) | | PPD (25 µg/ml) | |
|---|---|---|---|---|---|
|  |  | Net cpm | SI | Net cpm | SI |
| BCG | 6 | 15784 | 41.4 | 4346 | 12.1 |
|  | 6 | 15502 | 6.4 | 3119 | 2.1 |
|  | 6 | 13494 | 8.8 | 1413 | 1.8 |
| Mean +/− SEM | 6 | 14927 +/− 721 | 18.9 +/− 11.3 | 2959 +/− 850 | 5.3 +/− 3.4 |
| MYC1552 | 6 | 4381 | 11.1 | 8775 | 21.3 |
|  | 6 | 59445 | 16.6 | 1431 | 0.6 |
|  | 6 | 6336 | 4.4 | 2460 | 2.3 |
| Mean +/− SEM | 6 | 23387 +/− 18037 | 10.7 +/− 3.5 | 3268 +/− 2974 | 8.1 +/− 6.6 |
| MYC1551 | 6 | 17321 | 13.3 | 400 | 1.3 |
|  | 6 | 4750 | 10.9 | 677 | 2.4 |
|  | 6 | 63885 | 143.0 | 3811 | 9.5 |
| Mean+/− SEM | 6 | 28652 +/− 17986 | 55.7 +/− 43.6 | 1629 +/− 1093 | 4.4 +/− 2.54 |
| BCG | 9 | 36372 | 149.9 | 1125 | 5.6 |
|  | 9 | 50064 | 186.9 | 1519 | 6.6 |
| Mean +/− SD | 9 | 43218 +/− 6846 | 168.4 +/− 18.4 | 1322 +/− 197 | 6.12 +/− 0.5 |
| MYC1552 | 9 | 14150 | 94.1 | 293 | 2.9 |

TABLE 3-continued

Proliferation of lymphocyte from vaccinated guinea pigs to PPD.

|  |  | ConA (10 μg/ml) | | PPD (25 μg/ml) | |
| --- | --- | --- | --- | --- | --- |
| Group | Necropsy | Net cpm | SI | Net cpm | SI |
| MYC1551 | 9 | 25347 | 135.6 | 397 | 3.1 |
|  | 9 | 33211 | 124.3 | 796 | 4.0 |
|  | 9 | 50512 | 234.1 | 488 | 3.3 |
| Mean +/− SEM | 9 | 36357 +/− 7432 | 164.7 +/− 34.9 | 560 +/− 121 | 3.4 +/− 0.2 |

TABLE 4

Protective efficacy of the different vaccine strains against low-dose pulmonary challenge in guinea pigs.

| Group | Lung (Log10 Viable Mycobacteria) | Spleen (Log10 Viable Mycobacteria) |
| --- | --- | --- |
| BCG | 4.9 | 4.1 |
|  | 3.8 | 2.8 |
|  | 4.3 | 0 |
|  | 5.1 | 0 |
|  | 4.2 | 0 |
| Mean +/− SEM | 4.5 +/− 0.2 | 1.4 +/− 0.9 |
| MYC1552 | 4.7 | 4.7 |
|  | 5.0 | 4.0 |
|  |  | 5.0 |
| Mean +/− SEM | 4.8 +/− 0.2 | 4.6 +/− 0.3 |
| MYC1551 | 5.1 |  |
|  | 4.3 | 5.3 |
|  | 4.0 | 2.3 |
|  | 4.6 | 3.4 |
|  | 5.1 | 1.3 |
| Mean +/− SEM | 4.6 +/− 0.2 | 3.1 +/− 0.9 |
| unimmunized controls | 5.3 |  |
|  | 5.9 |  |
|  | 5.2 | 4.8 |
|  | 5.4 | 4.7 |
|  | 6.0 |  |
| Mean +/− SEM | 5.6 +/− 0.2 | 4.7 +/− 0.1 |

Thus, with the goal of developing a novel vaccine against tuberculosis, we constructed and evaluated the attenuation and protective efficacy of purC- auxotrophic mutant strains of M. tuberculosis and M. bovis BCG carrying a defect in their purine biosynthetic pathway. This approach was justified by the fact that attenuated strains are generally more potent than non-living vaccines in stimulating cell-mediated immune responses which are effective against intracellular pathogens (Brown et al., 1993), and because, in theory, they produce most of the antigens normally expressed in vivo by the pathogens. Thus, immune responses are stimulated in ways which closely resemble those detected during normal infection. Moreover, by constructing an auxotrophic strain derived from *M. tuberculosis,* one would derive a vaccine candidate antigenically identical to the pathogen against which protection was desired.

As shown for other purine auxotrophs of intracellular pathogens which reside inside vacuoles (McFarland & Stocker, 1987; O'Callaghan et al., 1988; Crawford et al., 1996), *M. tuberculosis* (MYC1551) and *M. bovis* BCG (MYC1552) purine deficient mutants were attenuated both in an in vitro macrophage model and in vivo in mice and guinea pigs. Since the introduction of the purC gene on a plasmid into the *M. tuberculosis* auxotroph fully restores its ability to replicate and lyse the macrophages, one can conclude that restriction for growth inside these cells is due to the insertional disruption of the purC gene alone and not to polarity affecting the expression of adjacent genes.

In contrast to what was observed with their respective parental strains, the number of MYC1551 in mouse bone-marrow macrophages did not increase over a 15 days period of time, but remained approximately constant, whereas the number of MYC1552 steadily decreased from the first day post-infection. In the absence of purine bases in the medium, most likely resembling the situation within the phagosomal compartment, both auxotrophs were unable to multiply. Thus, this difference in intracellular persistence between MYC1551 and MYC1552 probably reflects the different abilities of these *M. tuberculosis* and *M. bovis* BCG derivatives to resist phagocytic cells defenses and/or to make the phagosome in which they reside more hospitable.

The behavior of the auxotrophs in mice reflects the results obtained in isolated macrophages: the MYC1551 strain was progressively eliminated after a lag period of two to three weeks during which the number of cfu in all organs remained almost constant, whereas elimination of MYC1552 began immediately after the infection. Overall, both strains were eliminated at about the same rate from mice. In guinea pigs, fewer MYC1551 than BCG and no MYC1552 were found in the spleens three weeks post-immunization. Finally, based on data obtained from the macrophages and guinea pigs experiments in which the same infecting doses were used for all strains, it seems that both MYC1551 and MYC1552 are more attenuated than BCG.

Protection studies demonstrated that all three strains (BCG, MYC1551 and MYC1552) had equal statistically significant protective effects against an aerosol challenge with virulent *M. tuberculosis* H37Rv, as assessed by the reduction in cfu in the lungs of vaccinated guinea pigs. In the spleen, where a wider "protective window" is obtained, MYC1551 showed a significant protective effect as compared to unimmunized controls. This protective effect of MYC1551 appeared slightly less efficient than that conferred by BCG, although the difference was not statistically significant due to the heterogeneity of the guinea pigs responses to infection in every vaccination group. In the same organ, MYC1552 seemed to induce no protective response at all.

All three strains elicited non-statistically different strong DTH responses nine weeks post-infection, and stimulated PPD-induced lymphoproliferative responses six and nine weeks post-infection (with BCG the most potent in this respect after nine weeks), suggesting that both auxotrophs are able to induce cell-mediated immune responses of about equal intensity as those induced by the BCG vaccine. Therefore, the differences in the protective efficacies of BCG, MYC1551 and MYC1552 may have resulted from differences in the "quality" of the cellular immune responses they induce, rather than in the intensity. In fact, it is probable that an attenuated strain of mycobacteria needs to retain a limited ability to multiply in host cells and disseminate and persist within the host in order to be able to induce protective immune responses. This idea was originally pointed out by Kanai's work (1966), in which the protective efficacy of a streptomycin-dependent strain of *M. tuberculosis* was evaluated in guinea pigs and mice. In this system, streptomycin was used to induce the multiplication of the immunizing strain prior to challenge with virulent H37Rv tubercle bacilli. Experiments showed that only the *M. tuberculosis* that had multiplied during the immunization period conferred protection to the animals, with non-multiplying bacteria displaying poor protection.

Thus, the way an attenuated strain establishes an infection in the host, probably more than persistence in itself, seems to be important for inducing protective immune responses. Similar conclusions were drawn by O'Callaghan and collaborators (1988), in which the protective efficacies of a purA and of an aroA *Salmonella typhimurium* mutant, respectively deficient in the synthesis of adenine and aromatic amino-acids, were compared in relation to the infection they established in mice. These observations highlight the difficulty encountered when using live vaccines to reach the right balance between attenuation and immunogenicity, since over-attenuated bacteria may not produce in vivo some key antigens necessary for the induction of a protective immunity. The physiological state of the mutant bacilli might also influence the way their antigens are processed inside the macrophage and, thus, presented to the T lymphocytes.

The present work provides evidence that rationally attenuated strains of *M. tuberculosis* can protect guinea pigs against pulmonary tuberculosis. Finding an attenuated strain of the virulent tubercle bacillus which will have a greater efficacy than BCG seems reasonable if one considers that *M. tuberculosis* expresses additional highly immunogenic antigens such as ESAT 6 which the BCG lacks (Mahairas et al., 1996). However, this finding also seems dependent upon the level of attenuation of the vaccine candidate. Inactivating virulence genes instead of, or in addition to, "housekeeping" genes might be necessary to obtain a *M. tuberculosis* mutant which will multiply at a similar rate as BCG with the same level of attenuation.

In summary, a single, very simple system which can be used for easy mutagenesis of *M. tuberculosis* either by allelic exchange was designed. Using purC, a gene that was previously unable to mutate in *M. tuberculosis*, it was demonstrated that ts—SacB vectors can also be used for allelic exchange mutagenesis. All the clones obtained after a double-selection were indeed allelic exchange mutants. The *M. tuberculosis* purine auxotrophic mutant presents vaccmal potential (Fields, et al., 1986) and may also be used for the development of an IVET technology allowing the selection of mycobacterial genes preferentially expressed in vivo (Mahan et al., 1993; incorporated herein by reference). Provided that its function is dispensable to the cell, it is reasonable to assume that the same protocol should allow mutagenesis of virtually every gene of *M. tuberculosis* through gene exchange.

This new tool should greatly contribute to the genetic analysis of *M. tuberculosis* pathogenicity following Koch's postulates: it allows creation of deemed mycobacterial mutants by allelic exchange which was previously difficult, or even unfeasible. It opens the way not only to studying the roles in pathogenicity of defined mycobacterial genes which may or may not present similarities to known virulence factors from other bacterial pathogens, but also to the rational construction of attenuated strains which could be more effective than the BCG as antituberculous vaccines.

REFERENCES

Andersen, P. (1994) Effective vaccination of mice against *Mycobacterium tuberculosis* infection with a soluble mixture of secreted mycobacterial proteins. *Infect. Immun.* 62, 2536–2544.

Andersen, P., Andersen, A. B., Sorensen, A. L. & Nagai, S. (1995) Recall of long-lived immunity to *Mycobacterium tuberculosis* infection in mice. *J. Immunol.* 154, 3359–3372.

Arruda, S., Bornfim, G., Knights, R. Huima-Byron, T. & Riley, L. W. (1993) *Science* 261:1454–1457.

Azad, A. K., Sirakova, T. D., Rogers, L. M. & Kolattukudy, P. B. (1996) *Proc. Nat. Acad Sci.* USA 93:4787–4792.

Balasubramanian, V., Pavelka, M. S., Bardarov, S. S., Martin, J., Weisbrod, T. R., McAdam, R. A., Bloom, B. R. & Jacobs Jr., W. R. (1996) Allelic exchange in *Mycobacterium tuberculosis* with long linear recombination substrates. *J. Bacteriol.* 178, 273–279.

Bange, F. -C., Mazzaccaro, R. J., Balasubramanian, V., Bloom, B. R. & Jacobs Jr., W. R. (1996b) Leucine auxotrophy restricts growth of *Mycobacterium bovis* BCG but does not affect growth of *Mycobacterium tuberculosis* in SCID mice. In *Third international conference on the pathogenesis of mycobacterial infection*, pp. 33. Stockholm, Sweden.

Bange, F. C., Brown, A. M. & Jr., W. R. J. (1996a) Leucine auxotrophy restricts growth of *Mycobacterium bovis* BCG in macrophages. *Infect. Immun.* 64, 1794–1799.

Bardarov, S., Kriakov, J., Carriere, C., Yu, S., Vaamonde, C., Adam, R. A. M., Bloom, B. R., Hatfull, G. F. & Jr., W. R. J. (1997) Conditionally replicating mycobacteriophages: a system for transposon delivery to *Mycobacterium tuberculosis*. *Proc. Natl. Acad Sci* USA 94, 10961–10966.

Bartow, R. A. & McMurray, D. N. (1989) Vaccination with *Mycobacterium bovis* BCG affects the distribution of Fc receptor-bearing T lymphocytes in experimental pulnonary tuberculosis. *Infect. Immun.* 57, 1374–1379.

Bloom, B. R. & Murray, C. J. L. (1992) *Science* 257:1055–1064.

Bowe, F., O'Gaora, P., Maskell, D., Cafferkey, M. & Dougan, G. (1989) Virulence, persistence, and immunogenicity of *Yersinia enterolitica* 0:8 aroA mutants. *Infect. Immun.* 57, 3234–3236.

Brown, F., Dougan, G., Hoey, E. M., Martin, S. J., Rima, B. K. & Trudgett, A. (1993) *Vaccine design*. Chichester: John Wiley & Sons.

Cirillo, J. D., Barletta, R. G., Bloom, B. R. & Jacobs Jr., W. R. (1991) *J. Bacteriol.* 173:7772–7780.

Colditz, G. A., Brewer, T. F., Berkey, B. S., Wilson, M. E., Burdick, E., Fineberg, H. V. & Mosteller, F. (1994) Efficacy of BCG vaccine in the prevention of tuberculosis. *JAMA* 271, 698–702.

Collins, D. M., Kawakami, R. P., de Lisle, G. W., Pascopella, L., Bloom, B. R. & Jacobs Jr., W. R. (1995) *Proc. Nat. Acad Sci.* USA 92:8036–8040.

Crawford, R. M., Verg, L. v. d., Yuan, L., Hadfield, T. L, Warren, R. L., Drazek, E. S., Houng, H. S. H., Hammack, C., Sasala, K., Polsinelli, T., Thompson, J. & Hoover, D. L. (1996) Deletion of purE attenuates *Brucella melitensis* infection in mice. *Infect Immun.* 64, 2188–2192.

Curcic, R., Dhandayuthapani, S. & Deretic, V. (1994) *Mol. Microbiol.* 13:1057–1064.

Curtiss, III, Roy, (1990) *New Generation Vaccines*, pp. 161–165.

Dolin, P. J., Raviglione, M. C. & Kochi, A. (1994) Global tuberculosis incidence and mortality during 1990–2000. *Bulletin of the World Health Organization* 72, 213–220.

Falkow, S. (1988) *Rev. Infect. Dis.* 10:5274–5276.

Fields, P. I., Swanson, R. V., Haidaris, C. G. & Heffron, F. (1986) *Proc. Nat. Acad. Sci.* USA 83:5189–5193.

Grover, A. A., Kim, H. K., Wiegeshaus, E. H. & Smith, D. W. (1967) Host-parasite relationships in experimental airborne tuberculosis. II. Reproducible infection by means of an noculum preserved at −70° C. *J. Bacteriol.* 94, 832–840.

Guilhot, C., Gicquel, B. & Martin, C. (1992) *FEMS Microbiol. Lett.* 98:181–186.

Guilhot, C., Otal, I., van Rompaey, I., Martin, C. & Gicquel, B. (1994) *J. Bacteriol.* 176:535–539.

Guleria, I., Teitelbaum, R., McAdam, R. A., Kalpana, G., Jr., W. R. J. & Bloom, B. R. (1996) Auxotrophic vaccines for tuberculosis. *Nature Medicine* 2, 334–337.

Haslov, K., Andersen, A., Nagai, S., Gottschau, A., Sorensen, T. & Andersen, P. (1995) Guinea pig cellular immune responses to proteins secreted by *Mycobacterium tuberculosis*. *Infection and Immunity* 63, 804–810.

Hoiseth, S. K. & Stocker, B. A. D. (1981) Aromatic dependent *Salmonella typhimurium* are non-virulent and effective as live vaccines. *Nature* 291, 238–239.

Huygen, K., Content, J., Denis, O., Montgomery, D. L., Yawman, A. M., Deck, R. R., DeWitt, C. M., Orme, I. A., Baldwin, S., Souza, C. D., Drowart, A., Lozes, E., Vandenbussche, P., van Vooren, J. P., Liu, M. A. & Ulmer, J. B. (1996) Immunogenicity and protective efficacy of a tuberculosis DNA vaccine. *Nature Medicine* 2, 893–898.

Jackson, M., Berthet, F. X., Otal, I., Rauzier, J., Martin, C., Gicquel, B. & Guilhot, C. (1996) The *Mycobacterium tuberculosis* purine biosynthetic pathway: isolation and characterization of the purC and purL genes. *Microbiol* 142,2439–2447. Huygen, K. et al. (1996) *Nature Medicine*, 2(8):893–898

Jacobs Jr., W. R. (1992) *Immunobiol.* 184:147–156.

Kanai, K. (1966) Experimental studies on host-parasite equilibrium in tuberculosis infection, in relation to vaccination and chemotherapy. *Japan. J. Med Sci Biol.* 19, 181–199.

Kaufmann, S. H. E. & Embden, J. D. A. v. (1993) Tuberculosis: a neglected disease strikes back. *Trends in microbiology* 1, 2–5.

Levin, M. M., Hernington, D., Murphy, J. R., Morris, J. G., Losonsky, G., Tall, B., Lindberg, A., Svenson, S., Baqar, S., Edwards, M. F. & Stocker, B., (1987) *J. Clin. Invest.*, 79:888–902.

Mahairas, G. G., Sabo, P. J., Hickey, M. J., Singh, D. C. & Stover, K. (1996) Molecular analysis of genetic differences between *Mycobacterium bovis* BCG and virulent *M. bovis*. *J Bacteriol.* 178, 1274–1282.

Mahan, M. J., Slauch, J. M. & Mekalanos, J. J. (1993) *Science* 259:686–688.

McAdam, R., Guilhot, C. & Gicquel, B. (1994) in *Tuberculosis*, ed. Bloom, B. R. (ASM Press, Washington, DC), pp. 199–216.

McAdam, R. A., Weisbrod, T. R., Martin, J., Scuderi, J. D., Brown, A. M., Cirillo, J. D., Bloom, B. R. & Jacobs Jr., W. R. (1995) In vivo growth characteristics of leucine and methionine auxotrophic mutants of *Mycobacterium bovis* BCG generated by transposon mutagenesis. *Infect. Immun.* 63, 1004–1012.

McFarland, W. C. & Stocker, B. A. D. (1987) Effect of different purine auxotrophic mutations on mouse-virulence of a Vi-positive strain of *Salmonella dublin* and of two strains of *Salmonella typhimurium*. *Microbial Pathogenesis* 3, 129–141.

McMurray, D. N. (1994) Guinea pig model of tuberculosis. In *Tuberculosis. Pathogenesis, protection and control*, pp. 135–147. Edited by B. R. Bloom. Washington, DC: ASM.

Norman, B., Dellagostin, O. A., McFadden, J. & Dale, J. W. (1995) *Mol. Microbiol.* 16:755–760.

Noriega, Fernando R., Wang, J. Y., Losonsky, G., Maneval D. R., Hone, D. M. & Levin, M. M., (1994) *Infect Immun.*, 62(11):5168–5172.

O'Callaghan, D., Maskell, D., Liew, F. Y., Easmon, C. S. F. & Dougan, G. (1988) Characterization of aromatic- and purine-dependent *Salmonella typhimurium*: Attenuation, persistence, and ability to induce protective immunity in BALB/c mice. *Infect. Immun.* 56, 419–423.

Oettinger, T. & Andersen, A. B. (1994) Cloning and B-cell-epitope mapping of MPT64 from *Mycobacterium tuberculosis* H37Rv. *Infect. Immun.* 62, 2058–2064.

Orme, I. A. (1988) Induction of nonspecific acquired resistance and delayed-type hypersensitivity, but not specific acquired resistance, in mice inoculated with killed mycobacterial vaccines. *Infect. Immun* 56, 3310–3312.

Oyston, P. C. F., Williamson, E. D., Leary, S. E. C., Eley, S. M., Griffin, K. F. & Titball, R. W., (1995) *Infec. Immun.*, 63(2):563–568.

Pascopella, L., Collins, F. M., Martin, J. M., Lee, M. H., Hatfill, G. F., Stover, C. K., Bloom, B. R. & Jacobs Jr., W. R. (1994) *Infect, Immun.* 62:1313–1319.

Pelicic, V., Reyrat, J. -M. & Gicquel, B. (1996) *FEMS Microbiol. Lett.* 144:161–166.

Peficic, V., Reyrat, J. -M. & Gicquel, B. (1996) *J. Bacteriol.* 178:1197–1199.

Pelicic, V., Reyrat, J. -M. & Gicquel, B. (1996) *Mol. Microbiol.* 20:919–925.

Pelicic, V., Jackson, M., Reyrat, J. M., Jacobs, W. R., Gicquel, B. & Guilhot, C. (1997. Efficient allelic exchange and transposon mutagenesis in *Mycobacterium tuberculosis*. *Proc. Natl. Acad Sci.* USA 94, 10955–10960.

Quandt, J. & Hynes, M. F. (1993) *Gene* 127:15–21.

Reyrat, J. -M., Berthet, F. -X. & Gicquel, B. (1995) *Proc. Nat. Acad. Sci.* USA 92:8768–8772.

Romain, F., Laqueyrerie, A., Militzer, P., Pescher, P., Chavarot, P., Lagranderie, M., Auregan, G., Gheorghiu, M. & Marchal, G. (1993) Identification of a *Mycobacterium bovis* BCG 45/47- kilodalton antigen complex, an immunodominant target for antibody response after immunization with living bacteria. *Infect. Immun.* 61, 742–750.

Simmons, C. P., Hodgson, A. L. M. & Strugnell, R. A. (1997) Attenuation and vaccine potential of aroQ mutants of *Corynebacterium pseudotuberculosis*. *Infect Immun.* 65, 3048–3056.

Snapper, S. B., Melton, R. B., Mustapha, S., Kieser, T. & Jacobs Jr., W. R. (1990) *Mol. Microbiol.* 4:1911–1919.

Straley, Susan C. and Harnon, Paula A, (1984) *Infection and Immunity*, 45(3):649–654.

Weiss, D. W. & Dubos, R. J. (1955). Antituberculous immunity induced in mice by vaccination with killed tubercle bacilli or with a soluble bacillary extract. *J. Exp. Med.* 101, 313–330.

Wiegeshaus, E. H., McMurray, D. N., Grover, A. A., Harding, G. E. & Smith, D. W. (1970) Host-parasite relationships in experimental airborne tuberculosis. III. Relevance of microbial enumeration to acquired resistance in guinea pigs. *Am. Rev. Respir. Dis.* 102, 422–429.

Wiker, H. G. & Harboe, M. (1992) The antigen 85 complex: a major secretion product of *Mycobacterium tuberculosis*. *Microbiol Rev.* 56,648–661.

Young, D. B., Kaufmann, S. H. E., Hermans, P. W. M. & Thole, J. E. R. (1992) Mycobactenal protein antigens: a compilation. *Mo. Microbiol.* 6, 133–145.

We claim:

1. The recombinant mycobacterium strain MYC 1551 (C.N.C.M. No. I-1871).

2. The recombinant mycobacterium strain MYC 1552 (C.N.C.M. No. I-1872).

3. A recombinant mycobacterium strain of pathogenic origin capable of replicating in a macrophage of a host, said strain containing in its chromosome or on a plasmid a counterpart to a gene in the wild type mycobacterium coding for a protein necessary for the biosynthesis of a purine or a pyrimidine base, wherein said counterpart gene in the recombinant mycobacterium has been inactivated by at least one point mutation or by addition, deletion, or substitution of one or more base pairs, wherein said mycobacterium strain is selected from the group consisting of *M. Bovis*-BCG, *M. tuberculosis,* and *M. smegmatis,* and said inactivated gene is a purC or purL gene.

* * * * *

UNITED STATES PATENT AND TRADEMARK OFFICE
CERTIFICATE OF CORRECTION

PATENT NO. : 6,261,568 B1
DATED : July 17, 2001
INVENTOR(S) : Brigitte Gicquel et al.

It is certified that error appears in the above-identified patent and that said Letters Patent is hereby corrected as shown below:

<u>Title page,</u>
Item [75], Inventors,
Line 1, "Bridgitte" should read -- Brigitte --.

Item [57], ABSTRACT,
Line 8, "mycobacterium of this invention have" should read -- mycobacterium of this invention has --.
Line 10, "an protective" should read -- a protective --.

Signed and Sealed this

Twenty-ninth Day of January, 2002

Attest:

JAMES E. ROGAN
*Attesting Officer*  *Director of the United States Patent and Trademark Office*